United States Patent
Sellers et al.

(10) Patent No.: US 6,908,469 B2
(45) Date of Patent: Jun. 21, 2005

(54) COMPACT MAXILLARY DISTRACTOR

(75) Inventors: Timothy M. Sellers, Wayne, PA (US); John M. Noon, Paoli, PA (US); René Haag, Berwyn, PA (US)

(73) Assignee: Synthes (USA), Paoli, PA (US)

( * ) Notice: Subject to any disclaimer, the term of this patent is extended or adjusted under 35 U.S.C. 154(b) by 21 days.

(21) Appl. No.: 10/135,281

(22) Filed: Apr. 30, 2002

(65) Prior Publication Data

US 2002/0156485 A1 Oct. 24, 2002

Related U.S. Application Data

(63) Continuation-in-part of application No. 09/971,216, filed on Oct. 3, 2001, now abandoned.
(60) Provisional application No. 60/237,519, filed on Oct. 4, 2000.

(51) Int. Cl.$^7$ ................................. A61B 17/66
(52) U.S. Cl. ........................................ 606/105
(58) Field of Search ...................... 606/60, 69, 71, 606/105; 433/7, 17, 18

(56) References Cited

U.S. PATENT DOCUMENTS

| 4,144,643 A | 3/1979 | Krygier |
| 4,187,841 A | 2/1980 | Knutson |
| 4,482,318 A | 11/1984 | Förster |

(Continued)

FOREIGN PATENT DOCUMENTS

| DE | 4018273 | 1/1991 |
| DE | 4007306 | 5/1991 |
| DE | 4219156 | 12/1993 |
| DE | 29716635 | 12/1997 |
| DE | 29813087 | 7/1998 |
| DE | 29921046 | 6/2000 |
| DE | 20012536 | 7/2000 |
| DE | 20008796 | 9/2000 |
| DE | 20008797 | 9/2000 |
| EP | 0770359 | 5/1997 |
| EP | 1088520 | 4/2001 |
| FR | 2715291 | 7/1995 |
| FR | 2787698 | 6/2000 |
| WO | WO 97/20512 | 6/1997 |
| WO | WO 98/09577 | 3/1998 |
| WO | WO 99/04713 | 2/1999 |
| WO | WO 99/04715 | 2/1999 |
| WO | WO 00/33751 | 6/2000 |
| WO | WO 00/56235 | 9/2000 |
| WO | WO 01/41662 | 6/2001 |

*Primary Examiner*—Kevin Shaver
*Assistant Examiner*—Michael B. Priddy
(74) *Attorney, Agent, or Firm*—Jones Day

(57) ABSTRACT

The present invention provides an improved orthopedic system for the modification of the distance between the maxilla and zygoma. In a preferred embodiment, the system includes first and second footplates attached to an orthopedic device. The second footplate is attached to the zygoma, with the first footplate being mechanically coupled to the maxilla. This mechanical coupling is achieved either through attachment directly to the maxilla or by attachment to a construct wired to the patient's teeth. The orthopedic device, which may be a distractor, allows for modification of the distance between the maxilla and zygoma. The entire system can advantageously be placed intra-orally within a patient. In a preferred embodiment, the device does not increase in length upon activation. In another preferred embodiment, the second footplate is offset, allowing the actuator to be placed under the zygoma. Methods for using this novel orthopedic system are also disclosed.

92 Claims, 13 Drawing Sheets

U.S. PATENT DOCUMENTS

| | | | |
|---|---|---|---|
| 4,571,177 A | 2/1986 | Dahan | |
| 5,129,903 A | 7/1992 | Luhr et al. | |
| 5,147,358 A | 9/1992 | Remmler | |
| 5,314,426 A | 5/1994 | Pohl et al. | |
| 5,328,364 A | 7/1994 | Doyle | |
| 5,364,396 A | 11/1994 | Robinson et al. | |
| 5,540,687 A | 7/1996 | Fairley et al. | |
| 5,616,142 A | 4/1997 | Yuan et al. | |
| 5,681,313 A | 10/1997 | Diez | |
| 5,700,263 A | 12/1997 | Schendel | |
| 5,769,850 A | 6/1998 | Chin | |
| 5,807,382 A | 9/1998 | Chin | |
| 5,810,812 A | 9/1998 | Chin | |
| 5,829,971 A | 11/1998 | Razdolsky et al. | |
| 5,855,580 A | 1/1999 | Kreidler et al. | |
| 5,873,715 A | 2/1999 | Liou | |
| 5,885,283 A | 3/1999 | Gittleman | |
| 5,885,289 A | 3/1999 | Muller | |
| 5,885,290 A * | 3/1999 | Guerrero et al. | 606/71 |
| 5,895,387 A | 4/1999 | Guerrero et al. | |
| 5,902,304 A | 5/1999 | Walker et al. | |
| 5,906,644 A * | 5/1999 | Powell | 623/20.15 |
| 5,976,142 A | 11/1999 | Chin | |
| 6,086,365 A | 7/2000 | Fields | |
| 6,106,525 A | 8/2000 | Sachse | |
| 6,113,599 A | 9/2000 | Landsberger | |
| 6,139,316 A | 10/2000 | Sachdeva et al. | |
| 6,171,313 B1 | 1/2001 | Razdolsky et al. | |
| 6,176,859 B1 | 1/2001 | Muller | |
| 6,187,004 B1 | 2/2001 | Fearon | |
| 6,217,323 B1 | 4/2001 | Liou | |
| 6,241,517 B1 | 6/2001 | Williams | |
| 6,293,947 B1 | 9/2001 | Buchbinder | |
| 6,471,706 B1 * | 10/2002 | Schumacher et al. | 606/69 |

* cited by examiner

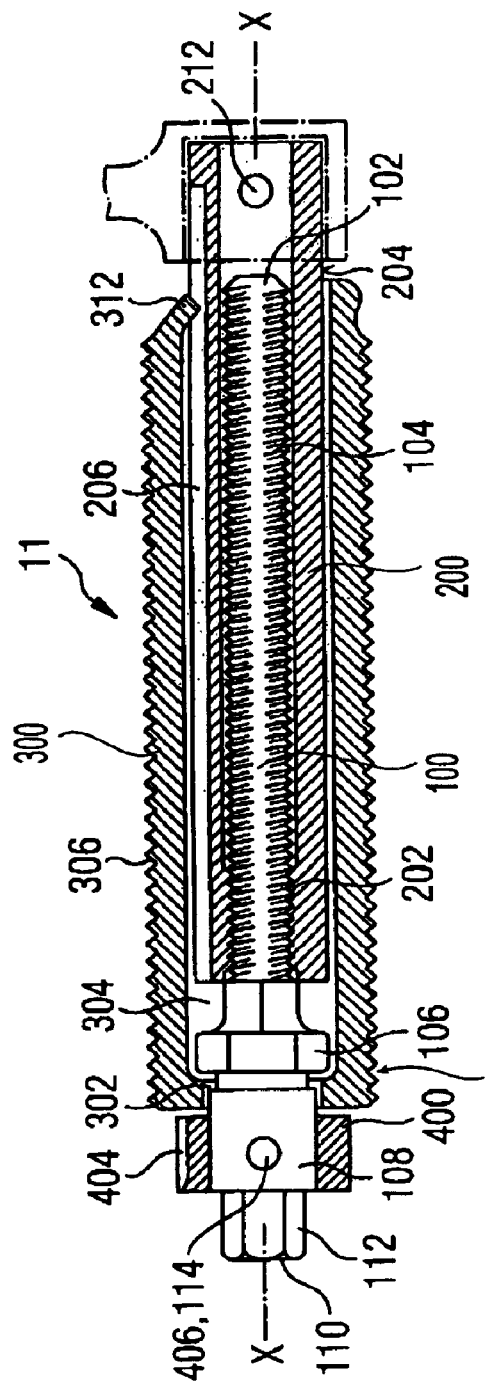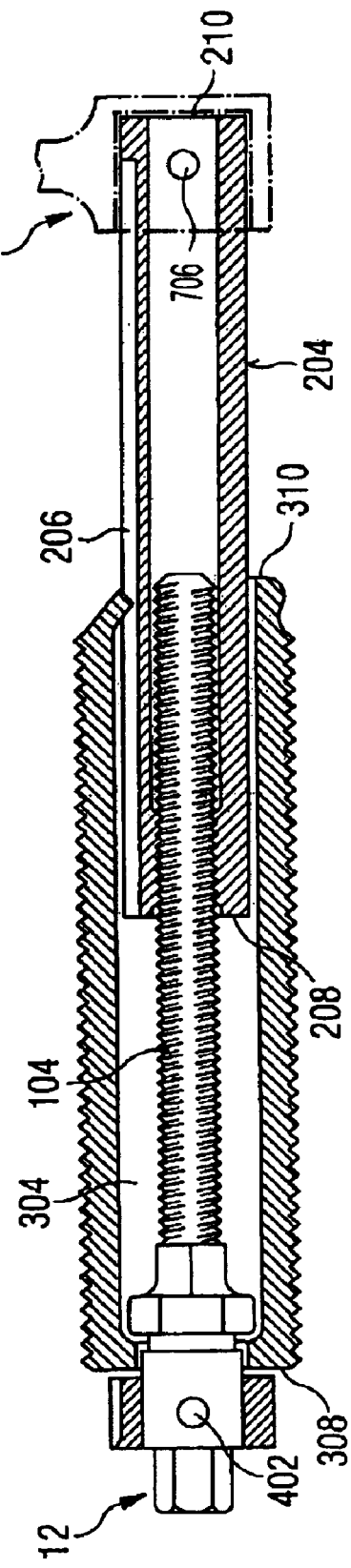
Fig. 3a
Fig. 3b

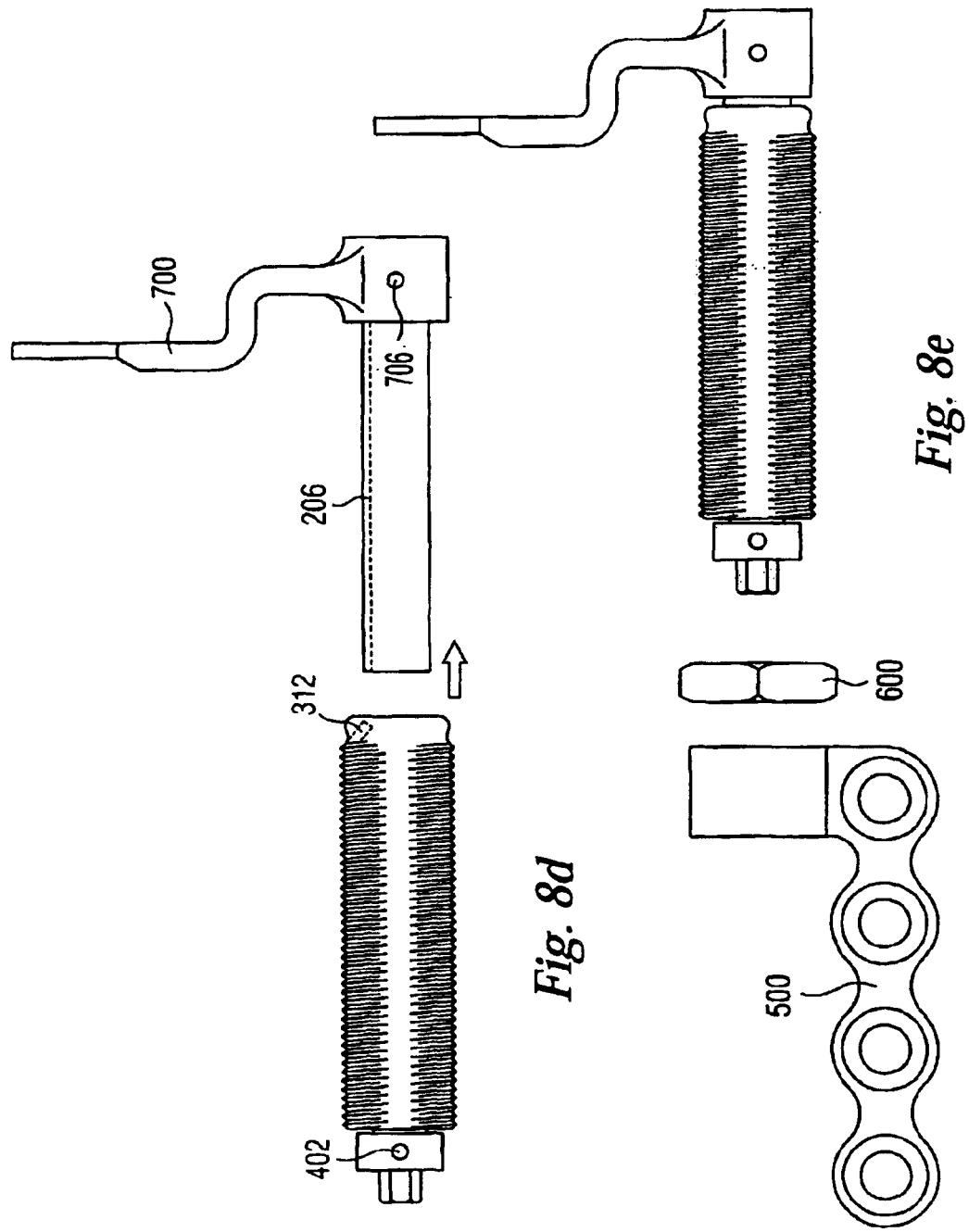

COMPACT MAXILLARY DISTRACTOR

CROSS-REFERENCE TO RELATED APPLICATIONS

This is a continuation-in-part of U.S. application Ser. No. 09/971,216 filed Oct. 3, 2001 now abandoned, which claims the benefit of U.S. Provisional Application No. 60/237,519 filed Oct. 4, 2000.

FIELD OF INVENTION

The present invention relates to an orthopedic system and, more particularly, to an improved orthopedic system wherein the device is used intra-orally in a patient to achieve a change in the position of the maxilla (upper jawbone) in relation to the zygoma (cheekbones).

BACKGROUND OF THE INVENTION

A variety of orthopedic devices, including bone reduction and distraction devices, are known in the art. Reduction and distraction devices (commonly referred to as reducers and distractors), are used to gradually adjust the relative orientation and spacing of the bone parts on opposing sides of a bone repair site. As used herein, "bone repair site" refers to any bone region which is bounded on opposing sides by relatively healthy bone regions to which orthopedic devices can be secured, such as an osteotomy (cutting of a bone) or a fracture.

Reducers and distractors typically consist of transcutaneous pins or screws secured in the bone on either side of the bone repair site together with a mechanism which allows controlled incremental adjustment of the distance between parts of the device on opposing sides of the bone repair site. Typically, distractors are used to perform distraction osteogenesis (the formation of bone). This procedure was perfected by the Russian orthopedic doctor, Gavriel Ilizarov. A typical procedure of this type involves at most an osteotomy completely separating the bone into two segments, or at least an incision of the cortical portion of the bone. Then, the bone segments on either side of the osteotomy (or the medullary or cancellous portion of the bone on either side of the incision) may be expanded. This gradual separation allows new bone to form in the osteotomy void. The distraction phase is followed by a consolidation phase, during which the distractor is held fixed, and the new bone growth gains strength. Following the consolidation phase, the distractor is removed from the patient.

One area in which distraction techniques are used is in treating patients diagnosed with maxillary hypoplasia (underdevelopment of the maxilla, or upper jawbone). One particular patient population with this condition is cleft-lip and -palate patients. The key reason for utilizing maxillary distraction to treat these patients is in the ability to successfully overcome the substantial soft tissue forces found in the maxillary region of these patients. Cleft-lip and -palate patients usually undergo surgery to correct their soft tissue deformities in early infancy. These procedures involve a great deal of soft tissue dissection, and leave the patient with significant scar tissue surrounding their maxillary region. As a result of the reduced elasticity of the scar tissue as compared to regular soft tissue, the maxilla is very often restricted from normal growth and can be very difficult to advance using conventional orthognathic surgery (surgery relating to treatment of the malpositioning of bones of the jaw). Maxillary distraction thus allows the tensile forces of the scar tissue to be overcome, and a greater advancement distance to be achieved, with a clinically supported expectation of a lesser degree of relapse (undesired movement of maxilla back towards its original position after treatment is finished).

An additional patient population that can take advantage of maxillary distraction is non-cleft palate patients having an A-P (Anterior-Posterior) maxillary deficiency of large magnitude. Typically, orthognathic procedures involving maxillary advancements are limited in the magnitude of the advancement of the maxilla due to the elastic properties of the surrounding soft tissues. Also, the larger advancements are more likely to require a bone graft to the site to ensure the long-term stability of the advancement. Using distraction for maxillary advancements can eliminate the magnitude limitations as well as the need for grafting for these patients.

Another benefit of performing maxillary distraction on cleft-lip and -palate patients is the ability to treat the maxillary hypoplastic patients at a younger age than with conventional orthognathic surgery. Early treatment of skeletal deformities has been gaining in popularity among craniofacial surgeons as a means of minimizing the negative psychosocial impact that craniofacial deformities have on children. Also, some surgeons believe that early correction of skeletal deformities can reduce the residual impact on surrounding tissues and structures, thus improving the overall result for the patient. See, for example, Steven Cohen, M.D., F.A.C.S., "Midface Distraction," Perspectives in Plastic Surgery, Vol. 11, No. 1.

However, the only available devices that can be used for maxillary distraction have external "halo-style" fixators that attach to the skull and to the maxilla by way of surgical wires affixed to an intra-oral appliance. One such known halo system is the KLS-Martin RED (Rigid External Distraction) system. Such a high profile external device is unsightly, and the psychosocial effects of wearing an external device is a major concern, especially with younger patients. An external device is also more subject to bumps and snags than one which is completely located within a patient's body. Accordingly, there is a need in the art to provide a device that can be used intra-orally to reliably perform distraction or reduction of the maxilla.

Furthermore, the known external fixators involve a large number of component parts and accordingly are complicated to install and adjust. Accordingly, there is a need in the art to provide a device that can be used to perform distraction or reduction of the maxilla that has a relatively low part count, and is simple both to install and adjust. Furthermore, there is a need for a distractor which occupies as little space as possible in the patient's mouth, even when the device is extended to its full length. In addition, there is a need to provide the installing surgeon with the flexibility to choose from multiple actuator lengths and footplate sizes, even after installation of the device has begun. Finally, there is a need to provide an intra-oral distractor whose alignment in the patient's mouth may be easily verified.

SUMMARY OF THE INVENTION

The present invention provides an orthopedic device for separating first and second bone segments. The device may comprise a first footplate comprising a bone attachment portion having a bone contacting surface which defines a first plant, and an actuator engaging portion. The device may further comprise a second footplate comprising a bone attachment portion having a bone contacting surface comprising a second plane which is substantially perpendicular to the first plane. The second footplate also may comprise an actuator attachment portion. The device may further comprise an actuator having a longitudinal axis and may be configured and adapted to be attached to the first bone segment using the first footplate and to the second bone segment using the second footplate, where the second plane is substantially perpendicular to the actuator longitudinal axis, and the actuator attachment portion lies at a predetermined distance from the second plane. This predetermined distance may be in a range from between about 1 millimeters (mm) to about 25 mm. More preferably, this predetermined distance may be in a range from between about 7 millimeters (mm) to about 12 mm.

The orthopedic device may be a distractor. The device may have one footplate configured and adapted to attach to a construct, the construct being mechanically coupled to the patient's teeth. At least one of the first and second footplates may be deformable to allow shaping to the surface of the bone segments.

The first and second footplates further may have at least one hole configured to accept at least one bone screw for attaching the respective footplate to bone. At least one footplate may be made of a bioresorbable material.

The device may further comprise a screw to removably fix the second footplate to the actuator, the screw having a head and a threaded portion. The second footplate attachment portion may further incorporate a bore having a shoulder and the actuator may further comprise a distal end having a threaded bore, and the second footplate actuator attachment portion engages the actuator, and the threaded portion of the screw is inserted through the second footplate attachment portion bore and engages the threaded bore of the actuator.

The device actuator may further comprise an advancement screw having external threads, and an outer sleeve having an axial slot and a second footplate engagement portion, the second footplate being coupled to the second footplate engagement portion. The first footplate may further comprise an actuator engaging portion having an internally threaded bore and an outer sleeve slot engaging portion, the first footplate bore interacting with the advancement screw, and the first footplate outer sleeve slot engaging portion interacting with the outer sleeve slot. The advancement screw and the outer sleeve may be associated such that only relative rotational movement about the longitudinal axis is permitted, so that rotation of the advancement screw causes movement of the first footplate with respect to the outer sleeve along the longitudinal axis. The first bone plate may be configured to attach to the maxilla and the second bone plate may be configured to attach to the zygoma.

The orthopedic device actuator may further comprise an outer surface, the actuator outer surface configured to engage a temporary alignment member for aligning the device prior to attachment to the bone segments. The device may be configured to be installed intra-orally. The actuatory outer surface may further comprise threads which match internal threads on a temporary alignment member. The actuator outer surface may also be keyed to the temporary alignment member.

In another embodiment, an orthopedic device is provided for modifying the distance between first and second bone segments of a patient, the system comprising a first footplate for subcutaneous implantation and attachment to the first bone segment, the first footplate having bone attachment and actuator attachment portions. A second footplate may be provided for subcutaneous implantation and attachment to the second bone segment, the second footplate having bone attachment and actuator attachment portions. An actuator having first and second ends also may be provided, wherein the first footplate actuator attachment portion engages the actuator between the actuator first and second ends, and the second footplate actuator attachment portion engages the actuator substantially adjacent to or at the second end, and wherein the second footplate actuator attachment portion is configured to be removably engageable with the actuator.

The device of this embodiment may be a distractor. The second footplate and actuator of the orthopedic device of this embodiment may also be keyed to prevent rotational movement between the footplate and the actuator. The device may further comprise a screw to removably fix the second footplate to the actuator, the screw having a head and a threaded portion. The second footplate attachment portion may further comprise a bore having a shoulder and the actuator may further comprise a distal end having a threaded bore, the second footplate actuator attachment portion engages the actuator, and the threaded portion of the screw is inserted through the second footplate attachment portion bore and engages the threaded bore of the actuator.

The second footplate of the distractor of this embodiment may be attached to the second bone segment and the first footplate may be configured and adapted to attach to a construct, the construct being mechanically coupled to the patient's teeth.

The footplates of the orthopedic device may be made of a bioresorbable material, and the actuator may be made of a non-bioresorbable material.

The device may further comprise and actuator having an externally threaded advancement screw, an outer sleeve having an axial slot and a second footplate engagement portion, the second footplate coupled to the second footplate engagement portion, the advancement screw and the outer sleeve associated to prevent relative axial translation and to permit relative rotation between the advancement screw and the outer sleeve. The actuator attachment portion of the first footplate may have an internally threaded bore, and an outer sleeve slot engaging portion. The first footplate bore may interact with the advancement screw, and the first footplate outer sleeve slot engaging portion may interact with the outer sleeve slot such that rotation of the advancement screw causes translational movement of the first footplate relative to the outer sleeve along the longitudinal axis.

A method is also provided for modifying the separation between the maxilla and zygoma of a patient comprising the steps of: making incisions for access to the maxilla and zygoma; mechanically coupling an orthopedic device of the present invention to the maxilla and zygoma so that at least a portion of the actuator is located behind the zygoma; closing the incision; performing distraction osteogenesis using the device; reopening the incision; removing the device from the patient; and closing the incisions. The method may comprise providing a distractor as the device. The method may comprise the further step of attaching the first footplate of the device to a construct which is attached to one or more of the patient's teeth. The method of the present invention may further comprise attaching the first and second footplates to the maxilla and zygoma using bioresorbable bone screws. The method may also comprise attaching the device second footplate to the zygoma such that the footplate bone contacting surface is in a range from between about 1 mm to about 25 mm from the actuator attachment portion. The method may comprise attaching an orthopedic device having first and second footplates at least a portion of which are bioresorbable so that only the actuator of the device is ultimately removed from the patient.

An additional method is provided for distracting the maxilla from the zygoma of a patient comprising the steps of: making at least one incision to expose the maxilla and zygoma; selecting first and second distraction assemblies comprising first and second footplates and an actuation assembly; aligning the first and second distraction assemblies on the patient's maxilla and zygoma; removing the first and second distraction assemblies from the patient; performing an osteotomy separating the maxilla from the zygoma; attaching the first and second distraction assemblies to the patient's zygoma using screws so that at least a portion of each assembly is located behind the zygoma; mechanically coupling the first and second distraction assemblies to the patient's maxilla using screws; closing the at least one incision, and leaving at least a portion of the distraction assembly of each device exposed; performing a distraction procedure, using the distraction assemblies to increase the separation of the maxilla from the zygoma; allowing time for consolidation; and removing the devices from the patient.

The method may also comprises selecting first and second distraction assemblies comprising first and second footplates made of bioresorbable material. The method may further comprise the additional step of installing first and second temporary alignment members on the first and second distraction assemblies, prior to aligning the distraction devices on the patient. The method may also comprise aligning the first and second distraction assemblies on the patient's maxilla and zygoma using the first and second temporary alignment members. The method may additionally comprise the step of, installing temporary attachment screws during the alignment step, and may further comprise the step of removing the temporary attachment screws after the alignment step. The method further may comprise the step of removing at least one of the temporary alignment members from its respective distraction assembly, prior to performing the osteotomy. The method also may comprise the additional step of re-attaching the at least one of the temporary alignment members to its respective distraction assembly prior to attaching the first and second distraction assemblies to the patient. The method may alternately comprise the step of attaching the first and second distraction assemblies to the patient using bioresorbable bone screws.

The method of the present embodiment may further comprise attaching at least one of the first footplates to at least one construct which is mechanically coupled to one or more of the patient's teeth. The method may also comprise removing only the first and second actuation assemblies, subsequent to consolodation, while leaving at least a portion of the footplates attached to the patient.

An assembly kit for an orthopedic device is also provided comprising at least one actuation assembly having first and second ends, and a longitudinal axis, a plurality of first footplates, each having a maxilla engaging portion and an actuator engaging portion, at least two of the first footplates having a different configuration; and a plurality of second footplates, each having a zygoma engaging portion and an actuator engaging portion, the zygoma engaging portion configured to permit at least a portion of the actuation assembly to be located behind the zygoma, at least two of the second footplates having a different configuration; wherein at least one of the first and second footplates are interchangeably removable from the actuation assembly to allow a surgeon to build a customized device to fit the anatomy of a particular patient.

The kit may include first footplate maxilla engaging portions and second footplate zygoma engaging portions having screw holes configured to accept bone screws, and the configuration of such screw holes is different for each first footplate. At least two of the first footplate maxilla engaging portions may have a different shape. At least two of the second footplate zygoma engaging portions further comprise a different shape. Each second footplate zygoma engaging portion may be configured to permit the actuation assembly to be located behind the zygoma by a different amount. The kit of the present embodiment may further comprise a screw to removably fix the second footplate to the actuator, the screw having a head and a threaded portion. Each second footplate actuator engaging portion may further comprise a bore and the at least one actuator further comprises a distal end having a threaded bore, each second footplate actuator attachment portion is configured to engage the at least one actuator, and the threaded portion of the screw may be inserted through the second footplate bore to engage the threaded bore of the at least one actuator. The kit may further comprise a plurality of temporary alignment elements configured to be removably engageable with the at least one actuation assembly to permit in-situ alignment of the orthopedic device.

BRIEF DESCRIPTION OF THE DRAWINGS

The features and advantages of the present invention will become more readily apparent from the following detailed description of the invention in which like elements are labeled similarly and in which:

FIGS. 3a and 3b are side views of the distraction assembly of the distractor illustrated in FIG. 2, in partial section and partial elevation view, showing the distractor at various stages of advancement;

FIGS. 8a to 8e are side views showing the successive steps in the assembly of the device illustrated in FIG. 2;

DETAILED DESCRIPTION OF PREFERRED EMBODIMENTS

The orthopedic device of the present invention is discussed herein with reference to a preferred embodiment adapted to be used in a linear distraction of the maxilla from the zygoma.

Figure 1:
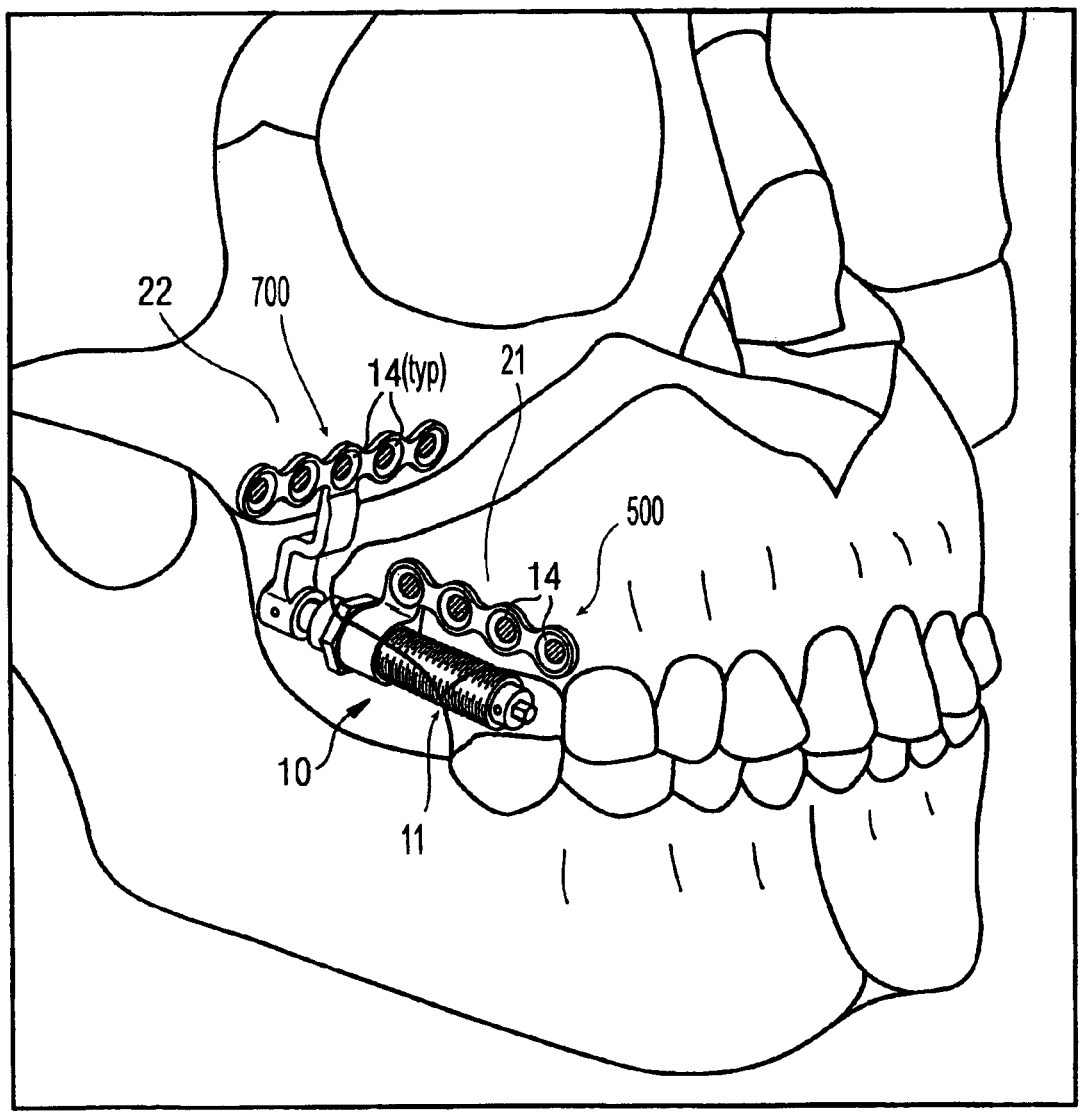
FIG. 1 is a perspective view of an embodiment of the present orthopedic system adapted for use on the maxilla, illustrating a distractor attached to the maxilla and zygoma.
Figure 2:
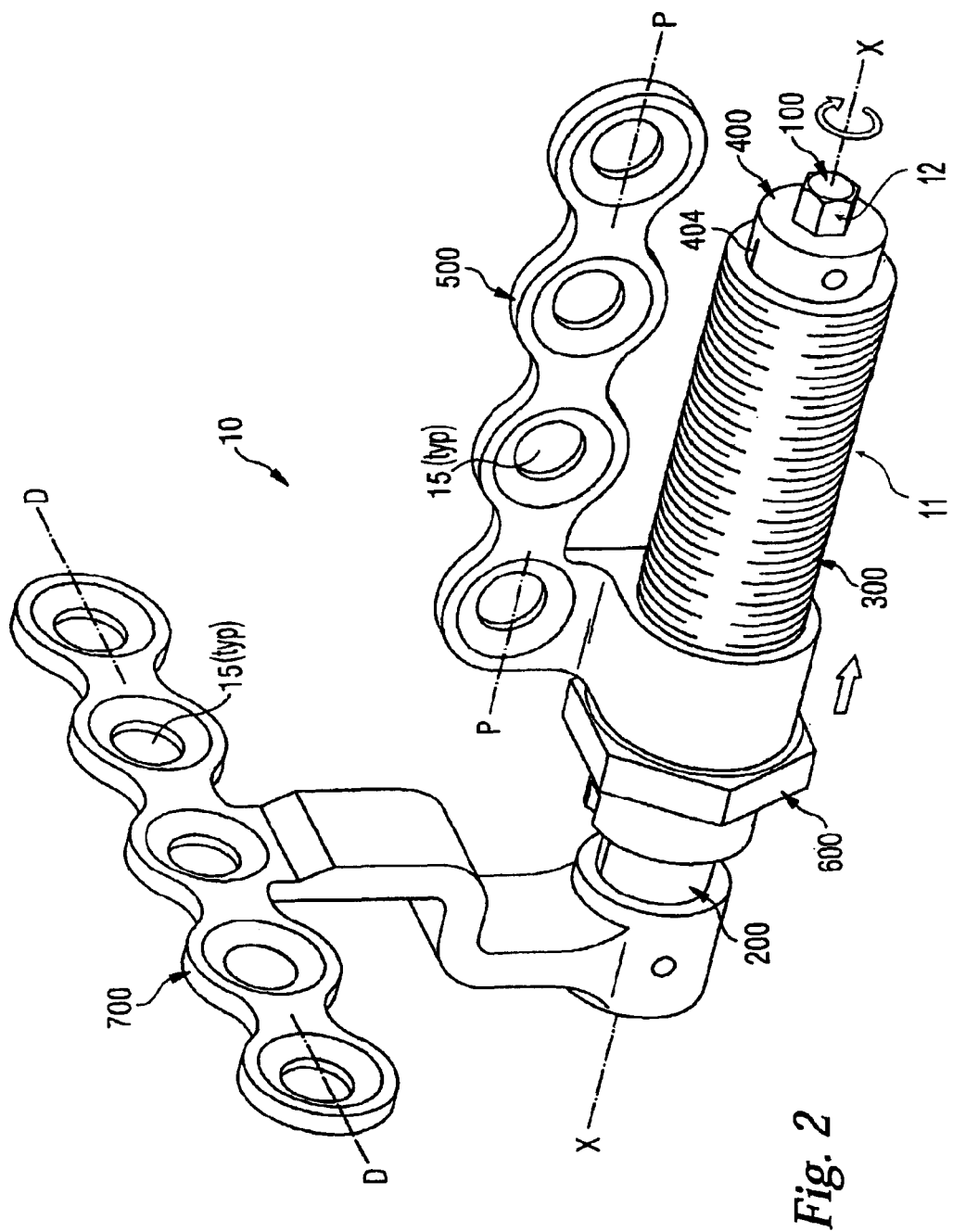
FIG. 2 is a perspective view of a distractor of the system as illustrated in FIG. 1.

As seen in FIGS. 1, 2, and 3a, the orthopedic system 10 generally consists of distraction assembly 11 and anchors in the form of proximal and distal bone plates 500 and 700, respectively. The distraction assembly 11 has a proximal, or adjustment end 12 and a distal end 13. The orthopedic system 10 is affixed to maxilla 21 and zygoma 22 by bone screws 14 which are inserted though screw-holes 15 in footplates 500 and 700. In use, the entire orthopedic system 10 is implanted so that the distal bone plate 700 is attached to the zygoma 22 and the proximal bone plate 500 is attached to the maxilla 21, with the distraction assembly 11 nestled within the buccal sulcus. It will be understood that with reference to the various elements of the present invention, the term proximal is used to refer to the end of the device associated with the proximal end of the distraction assembly 12 that extends outwards away from the patient's zygoma 22. The term distal is used to refer to the other end of the device 13.

Turning now to the details of the orthopedic system 10 as best illustrated in FIGS. 2, 3a, and 3b, the distraction assembly 11 generally consists of a lead screw 100, an inner sleeve 200, and an outer sleeve 300. As described in detail below, lead screw 100 is journaled within outer sleeve 300, such that screw 100 can rotate, but not translate linearly (axially), relative to outer sleeve 300. Inner sleeve 200 has internal threading 202 which interacts with the external threading 104 on screw 100. Conversely, the interaction of the inner and outer sleeves, as discussed below, is such that they can translate linearly with respect to each other, but cannot rotate relative to each other. Thus, in the assembled distraction assembly 11, rotation of lead screw 100 is translated into linear motion of the inner sleeve 200 relative to the lead screw and outer sleeve, like a nut being driven on a bolt, causing telescopic expansion or contraction of the overall assembly 11.

Lead screw 100 has a distal shaft portion 102 provided with external screw threading 104, an enlarged-diameter intermediate portion 106, a proximal shaft portion 108, and a proximal, or adjustment end 110. Adjustment end 110 is provided with a tool interface 112, such as a hexagonal surface that can be driven by a standard hexagonal driving tool.

Inner sleeve 200 is provided with internal threading 202 along at least part of its length. The internal threading matches the external threading 104 on screw 100. The inner sleeve 200 has an exterior surface 204 which is generally smooth except for longitudinal slot 206 (shown in FIG. 4) which extends from the proximal end 208 of the sleeve towards the distal end 210.

Figure 4:
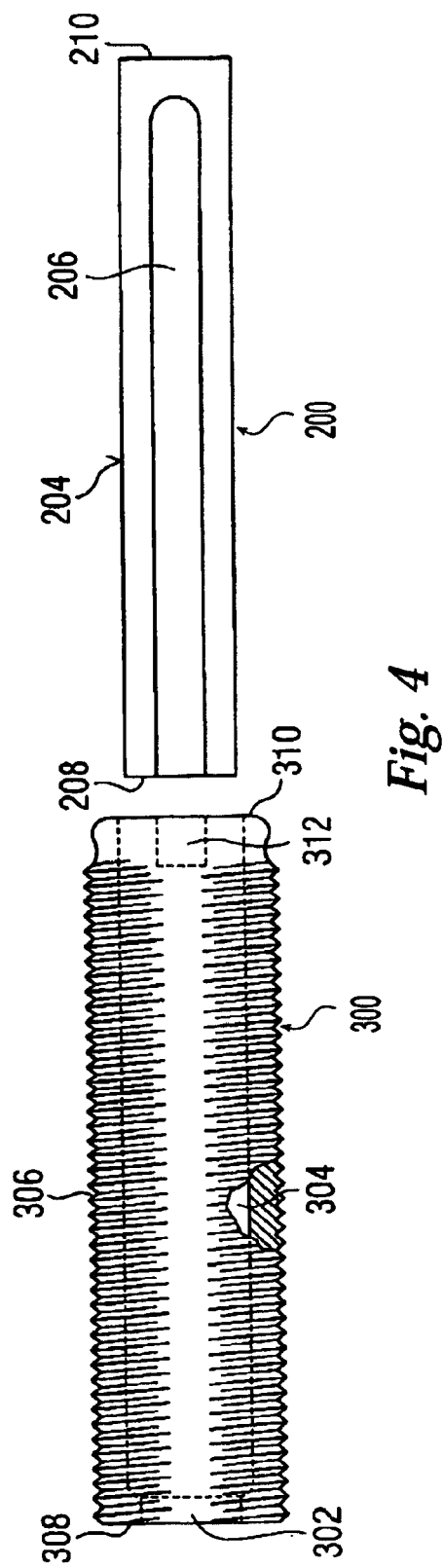
FIG. 4 is a top plan view of the inner sleeve and the outer sleeve of the distractor illustrated in FIG. 2.

As best seen in FIG. 4, the outer sleeve 300 has two different inside cavity portions. The proximal cavity portion 302 has an inside diameter sized so as to (rotatably) slidably accept the proximal shaft portion 108 of the screw 100. The distal cavity portion 304 has an inside diameter sized so as to (axially) slidably accept the inner sleeve 200. The external surface of the outer sleeve 306 is preferably threaded along most of its length except for the distal end 310.

A mechanism is provided to prevent rotation but allow translation of the inner sleeve 200 in relation to the outer sleeve 300. In the illustrated embodiment, this is accomplished by having a portion of the distal end of the outer sleeve 310 formed into a "key" 312 which is sized to fit the longitudinal slot 206 of inner sleeve 200. This can be accomplished by crimping the distal end by application of a force, by an appropriately-shaped tool, sufficient to permanently deform a portion of the distal end. Alternatively, a pin could be fixed in a though hole in the wall of the distal end, flush with the outer surface and extending radially inward, the inner end fitting in the longitudinal slot 206.

Lead screw 100 is journaled within the outer sleeve 300, so as to allow rotation of the lead screw 100 in relation to outer sleeve 300 but preventing translational motion. In a preferred embodiment, the journaling is accomplished according to the following. The proximal shaft portion 108 of lead screw 100 is slidably received within the proximal cavity portion 302 of the outer sleeve 300, such that screw 100 is free to rotate relative to the outer sleeve 300. A region of the proximal shaft portion 108, and the adjustment end 110 of screw 100, extend out from the proximal end 308 of the sleeve. A collar 400 is attached to the screw on the extending region of the proximal shaft portion, for example, by inserting pin 402 through matching holes 406 and 114 in the collar and proximal shaft portion, respectively. The collar 400 and the enlarged-diameter intermediate shaft portion 106 "sandwich" the proximal end 308 of outer sleeve 300, thereby preventing axial translation of the screw 100 relative to outer sleeve 300. In this way, screw 100 is effectively journaled within the outer sleeve 300.

The collar 400 also has a marking, such as an indentation, that acts as a visual reference mark 404. Since the collar rotates in conjunction with the advancement screw, the reference mark 404 gives the user of the device an easily usable visual means to measure the amount of rotation that the lead screw undergoes when it is adjusted. Knowing the thread pitch of the device, the user can easily convert angular displacement of the mark into linear advancement of the device. Other visual marking methods can be used, including the imprinting of marks on the surface of the collar.

Figure 5:
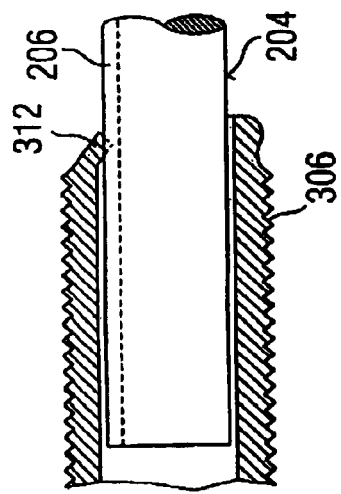
FIG. 5 is a sectional side view of the inner sleeve and the outer sleeve of FIG. 4 interacting with each other.

The internal threading 202 of inner sleeve 200 interacts with the external screw threading 104 of the lead screw 100, while at the same time the smooth exterior surface 204 of the inner sleeve is in sliding relation with the smooth inner surface of the distal cavity portion 304 of the outer sleeve. FIG. 5 illustrates how key 312 of the outer sleeve interacts with the longitudinal slot 206 to form a keyway. It will be appreciated that the interaction of longitudinal slot 206 and key 312 form a keyway which prevents relative rotation of the sleeves about the longitudinal axis X—X of the device (designated X—X in FIG. 3a), while freely permitting sliding, telescoping movement of the inner sleeve 200 relative to the outer sleeve 300.

The system provides a mechanism whereby the distractor is anchored or affixed to the patient, for example, by proximal and distal footplates 500 and 700, which are best understood by reference to FIG. 2. The footplates are provided with screw holes 15 to accept the bone screws 14 (shown in FIG. 1) which affix the device to the bone on either side of the patient's bone repair site. These holes are preferably countersunk to reduce the height of projection of the screw heads above the footplate surface after the device is fully implanted. The footplates have bottom coupling surfaces 506 (shown in FIG. 6) and 710 (shown in FIG. 7) which may be flat or preferably may be shaped to conform to the contours of the bone to which it is being attached. As discussed in detail below, the coupling surfaces are bone-contacting surfaces when the footplates are attached directly to the patient's bone, or may be construct-contacting surfaces when the footplate is attached to a construct which is in turn mechanically coupled to the patient's bone.

Footplates 500 and 700 serve as the anchors, and can be made from any biocompatible material such as metal, plastic, or composites. For example, the footplates may be made of titanium or titanium alloy. The choice of material from which to construct the footplates is a routine design matter which depends purely on the particular medical application in which the system according to this invention is used. In a preferred embodiment, the footplates are bone plates made of stainless steel. Experiments have shown that stainless steel provides the necessary strength while at the same time being malleable enough to (i) allow for adjustments to the footplates by bending them, and (ii) withstand the cyclic loading inherent in the jaw area.

Figure 6:
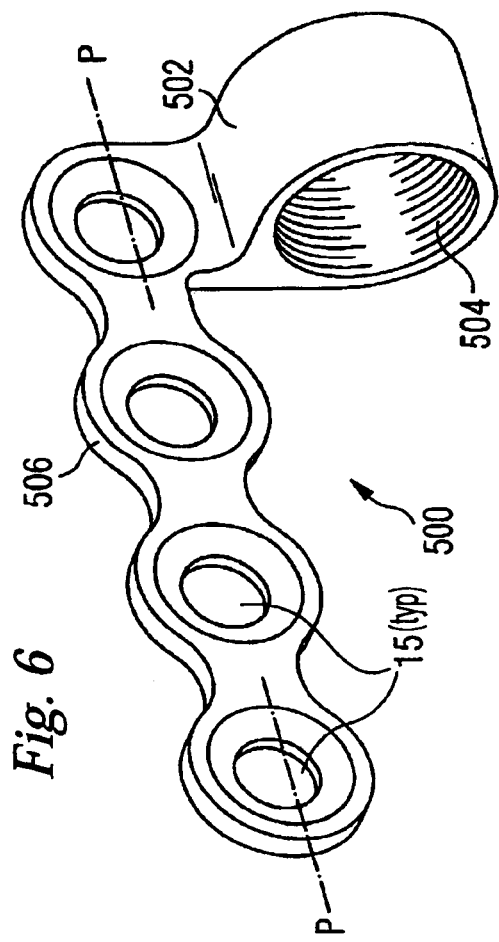
FIG. 6 is a perspective view of the proximal footplate illustrated in FIG. 2.

As shown in FIG. 6, the proximal footplate 500 has a device-connecting portion 502 comprising an internally-threaded bore 504 which accepts the threading on the external surface 306 of the outer sleeve 300. The internally-threaded bore 504 of the proximal footplate interacts with the external surface 306 of outer sleeve 300, so that the orientation and separation of the two footplates in relation to each other can be modified as needed, by screwing the sleeve 300 into the bore 504. Once the desired orientation and separation is achieved, proximal footplate 500 is locked into position by tightening locking nut 600 (shown in FIG. 2) against it, providing sufficient frictional force to keep the footplate in place.

Figure 7:
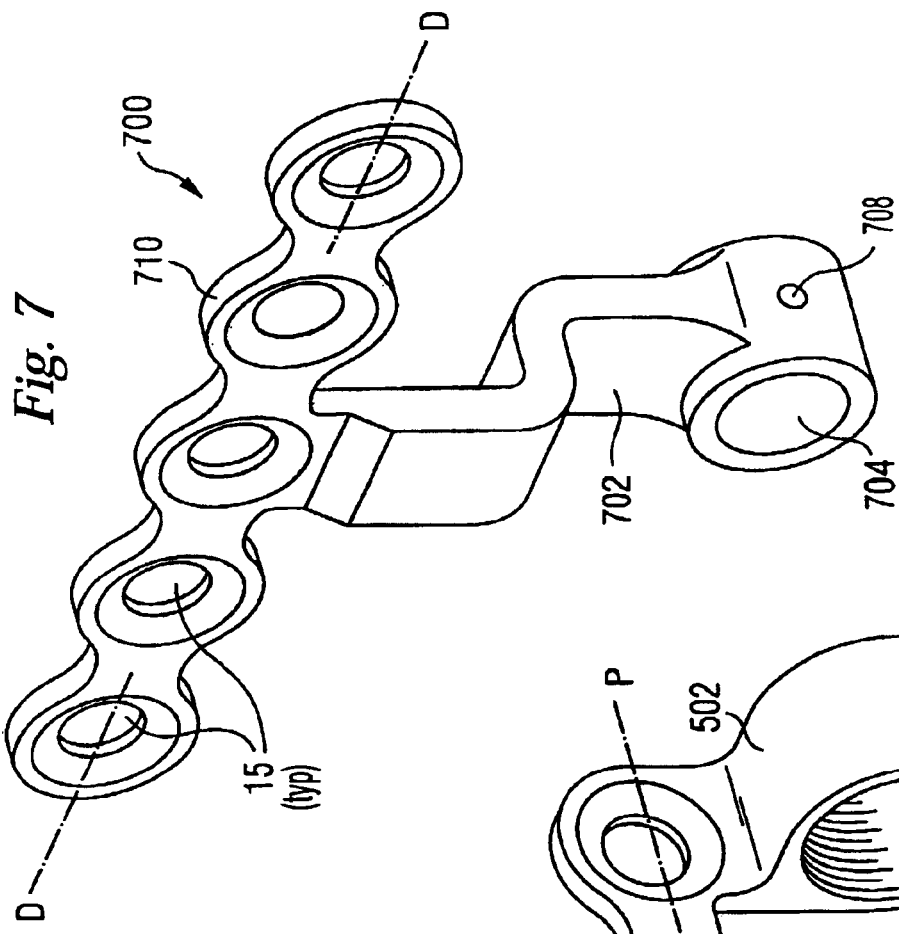
FIG. 7 is a perspective view of the distal footplate illustrated in FIG. 2.

As shown in FIG. 7, the distal footplate 700 has a device-connecting portion 702 comprising a bore 704 with a diameter that will accept inner sleeve 200. The distal footplate is attached to the distal end of inner sleeve 210, for example, by pressing the two together, and inserting a pin 706 through holes 708 and 212.

As best illustrated in FIG. 2, the proximal footplate 500 is oriented so that line P—P is generally parallel to axis X—X of the distraction assembly 11. It is also offset above and to either side of the distraction assembly 11, depending on which side of the patient the assembly is to be implanted. When placed on the right side of the patient, the footplate 500 is offset to the left of the distraction assembly 11, and vice-versa. FIG. 2 shows the right-side orientation of the footplate, while FIG. 6 shows the left-side orientation. The distal footplate 700 is oriented so that line D—D is generally orthogonal to and above axis X—X of the distraction assembly 11.

The above-described geometry of footplates 500 and 700 has been found to provide a good combination of accessibility to the screws and holding strength when the device of the present invention is used in the distraction of the maxilla. However, it is to be understood that the precise location of the screw holes and the contoured shape and orientation of plates 500 and 700 as seen in FIGS. 2, 6, and 7 are not a critical aspect of the invention; other screw hole placements, plate shapes, and plate orientations could be used without departing from the spirit and scope of the present invention.

Figure 8A:
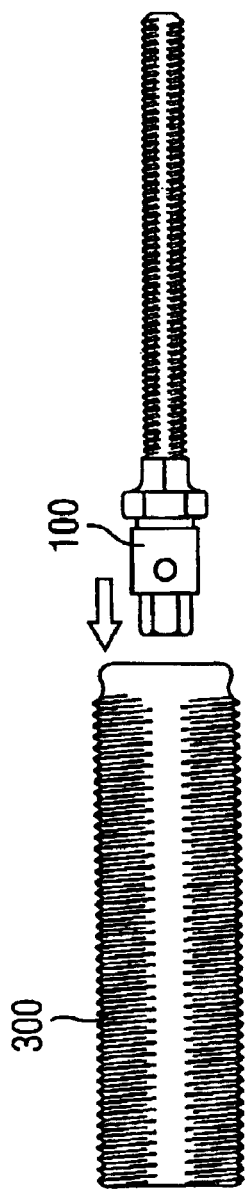
Figure 8C:
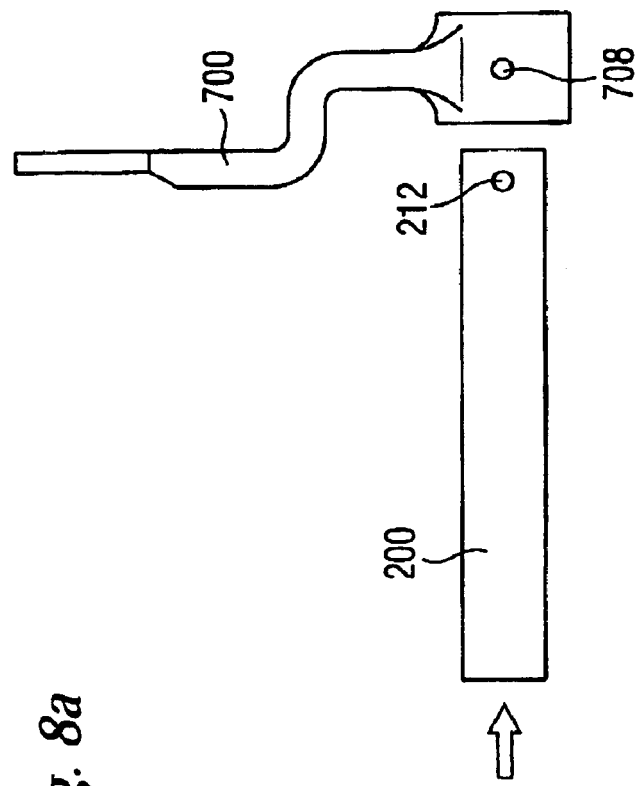
Figure 8B:
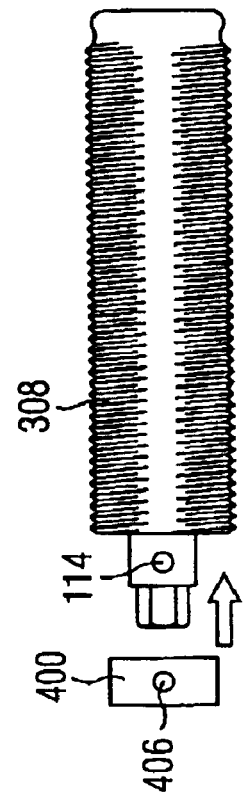

The assembly of the orthopedic system is best understood by reference to FIGS. 8a through 8e. To assemble the system, the lead screw 100 is first inserted into the outer sleeve 300, as shown in FIG. 8a. The collar 400 is then installed on the region of the proximal shaft portion 108 which extends out from the proximal end 308 of the outer sleeve 300, as shown in FIG. 8b. The collar 400 is captivated on the shaft by pressing pin 402 though matching holes in the collar 406 and proximal shaft portion 114. The distal footplate 700 is pressed onto the distal end 210 of inner sleeve 200, as shown in FIG. 8c, and captivated on the shaft by pressing pin 706 through matching holes 708, 212 in the footplate and the distal shaft portion, respectively. The lead screw is then threaded into inner sleeve 200, as shown in FIG. 8d, care being taken that the longitudinal slot 206 on sleeve 200 is properly engaging key 312. Nut 600 and proximal footplate 500 are then threaded onto outer sleeve 300, as shown in FIG. 8e.

The device of the present invention is normally used in pairs, one for each side of the patient's face. In order to use the device of the present invention in a maxillary distraction procedure, the surgeon makes an incision, fits the devices to the patient, temporarily removes the devices in order to perform a LeFort I osteotomy (the separation of the maxilla from the rest of the midface), attaches the devices, performs distraction and consolidation, then permanently removes the devices.

To implant the device, a maxillary vestibular incision is made on the side of the patient's mouth, so that the periosteum can be elevated to expose the maxillary and zygomatic bone. The assembled device is placed in the proper location and checked for the proper fit. Although the footplates are generally pre-shaped to be oriented in the proper manner, adjustments can be made to the footplates by bending them, for example, with a set of pliers. The distal footplate is then fastened to the zygoma with bone screws 14, using a number sufficient to provide the necessary stability and strength. In a preferred method, the screws are self-tapping, so no pre-tapping of the bone is required. If needed, excess material in the footplate can be removed. For example, if not all of the screw holes need to be used, the portion of the footplate having the unused holes may be clipped off. The anterior footplate is then attached in the same manner. The same procedure is then repeated on the other side of the patient.

The doctor then sketches out the planned osteotomy (typically a LeFort I osteotomy), making allowances for the distraction devices. The devices are removed, the osteotomy is performed, and the devices are put back into place. The incision is then closed, leaving the distraction assemblies exposed, but within the patient's mouth.

The distraction osteogenesis procedure is performed by turning the lead screws on each device using the tool interface 112. It will be understood by reference to FIG. 1 (which does not illustrate soft tissue) that the distal end of the devices, where tool interface 112 is found, is easily accessible in the intra-oral region, between the patient's cheek and gum. Counter-clockwise rotation of the screw will result in axial lengthening of the device, resulting in a distraction force being communicated to the bones through the footplates. The reference mark 404 can be used to measure the changes in advancement precisely. Generally, distraction progresses at a rate of 1–2 mm per day until full advancement is achieved. The advancement phase is followed by a consolidation phase, with a duration of at least twice as long as that of the advancement phase. The devices are then removed in a separate surgical procedure.

In another preferred embodiment, the proximal footplates 500 of the devices are not attached to the patient's maxilla 21, but rather to a construct, such as a dental splint, which is attached to the maxilla 21. A typical dental splint may consist of a disk of acrylic fitted or wired to the patient's teeth. Except for the differences described, this alternative method of treatment is the same as that used in the normal course of treatment. This embodiment can be used when the maxilla 21 of the patient cannot support the bone screws 14 used to support the footplates 500. This is often the case with cleft-lip or -palate patients, who often have large voids in the maxilla 21 where bone should be present. It may also be the preferred embodiment for treating younger patients, due to the presence of un-erupted tooth buds which might be damaged by bone screws 14.

It should be emphasized that the above described embodiments of methods to attach the device to the patient are merely specific examples for mechanically coupling the device to the zygoma and maxilla. The device footplates may be attached directly to the patient's bone. Alternatively, they may be attached to one or more constructs, which constructs are attached to the patient's bone. Indeed, the constructs do not necessarily need to be directly attached to the patient's zygoma or maxilla, but rather may be attached to the patient's teeth. What is important is that the device is mechanically coupled to the zygoma and the maxilla with sufficient rigidity in order to reliably perform the distraction. Alternately, the device may be implanted using circummaxillary wiring, in which wire is passed around the bony structure of the maxilla, to provide a firm anchorage for the device.

Figure 9A:
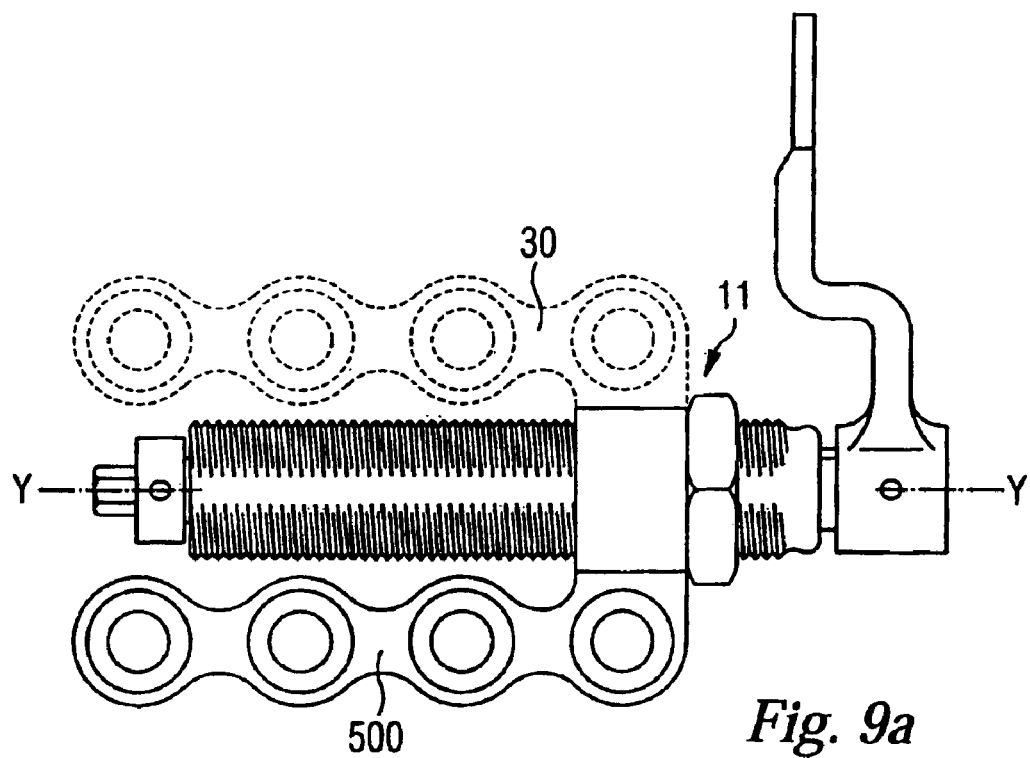
FIGS. 9a and 9b are side and front views, respectively, of the system as illustrated in FIG. 2, when used in an alternative method of treatment.
Figure 9B:
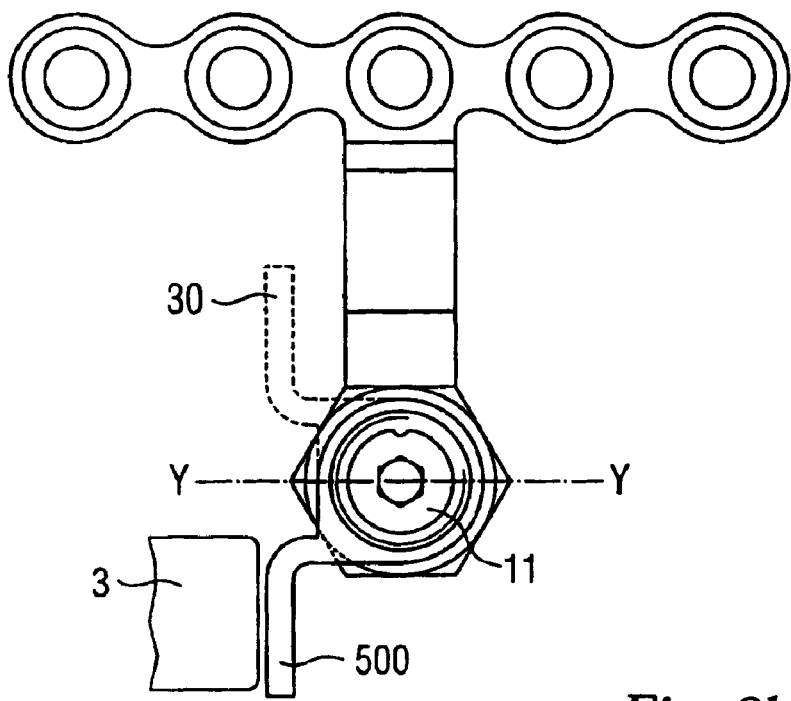

FIGS. 9a and 9b shows the device as it would be implanted on the left side of a patient using this embodiment. The orientation of the proximal footplates 500 is mirrored from its normal orientation 30 about the horizontal plane denoted by Y—Y. That is, for the device used on the left side of the patient, the footplate 500 is positioned below and to the right of the distraction assembly 11, as seen in FIGS. 9a and 9b. In practice, this may be done by simply rotating the footplate 500 one hundred eighty degrees (180°) about the X—X axis (as described in FIG. 3a), and switching the side of the patient's face to which the device is implanted. Put another way, the footplate 500 used on the right side of the patient when attaching the device directly to the maxilla 21 is the same one used on the left side when attaching the device to a dental splint, and vice-versa. This a orientation is preferred for the dental splint method because it places the footplate and screw holes closer to the horizontal plane created by the chewing surfaces of the teeth, which is the preferred position for attachment of the footplate to a dental splint. FIG. 9b shows a portion of the splint 3 in relation to the footplate 500.

In another preferred embodiment, the footplates and/or bone screws may be made from a bioresorbable material, and are detachable from the distraction assembly. This allows easy shaping of the footplates (when heated prior to insertion, for example by soaking in hot water). After distraction and consolidation have been completed, the bioresorbable footplates are detached from the distraction assembly and the incisions are closed, leaving the footplates and bone screws in place, to eventually be absorbed into the body. This provides the advantage of not having to perform a second surgical procedure to access the screws to remove the footplates. By reducing the number of surgical procedures required, the unavoidable risk and possible complications associated with any surgery is reduced. The bone screws should be made of a material that takes at least as long to absorb as the material the footplates are made of, thus ensuring that the footplates are secured until absorbed fully by the body.

Figure 10:
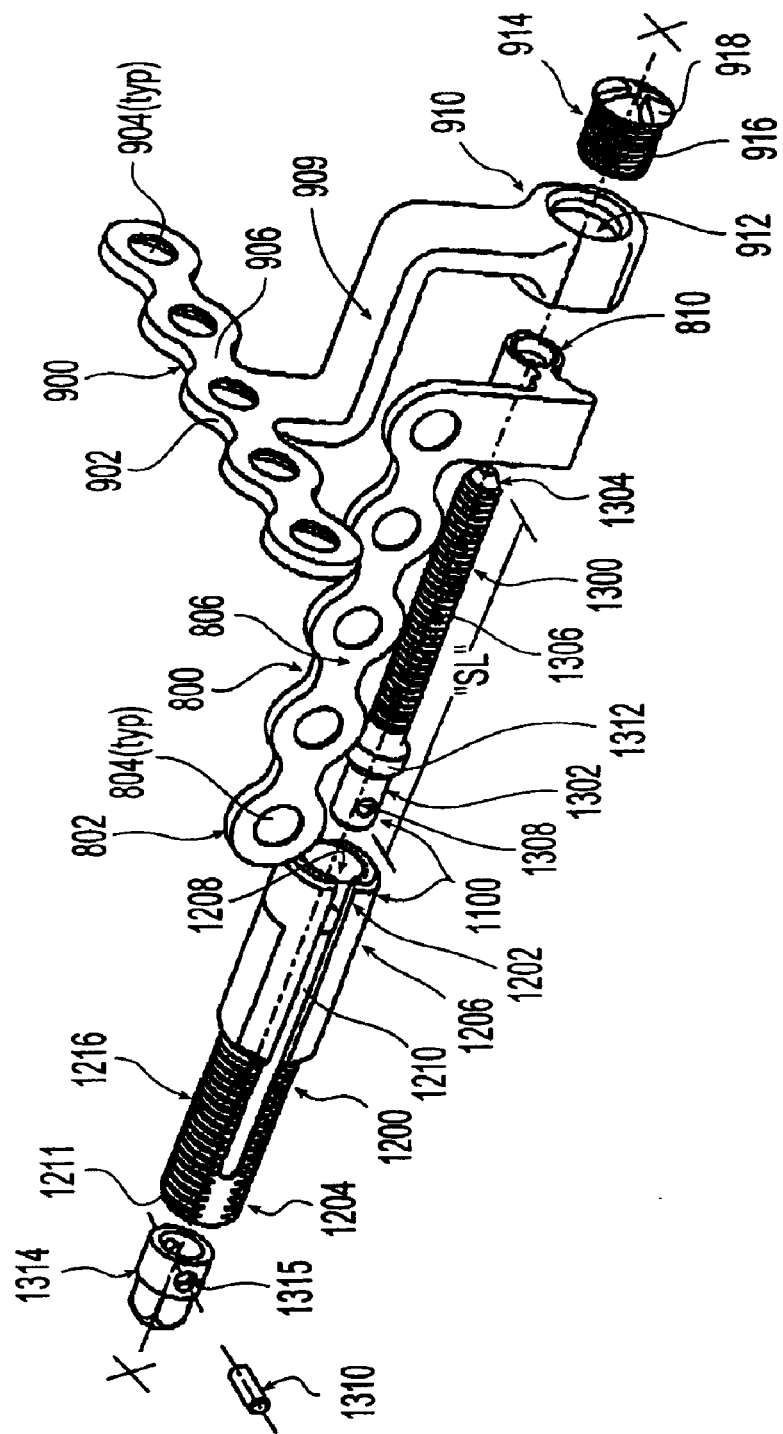
FIG. 10 is an exploded perspective view of an embodiment of the present orthopedic system, illustrating a compact intra-oral distractor for attachment to the maxilla and zygoma.
Figure 11A:
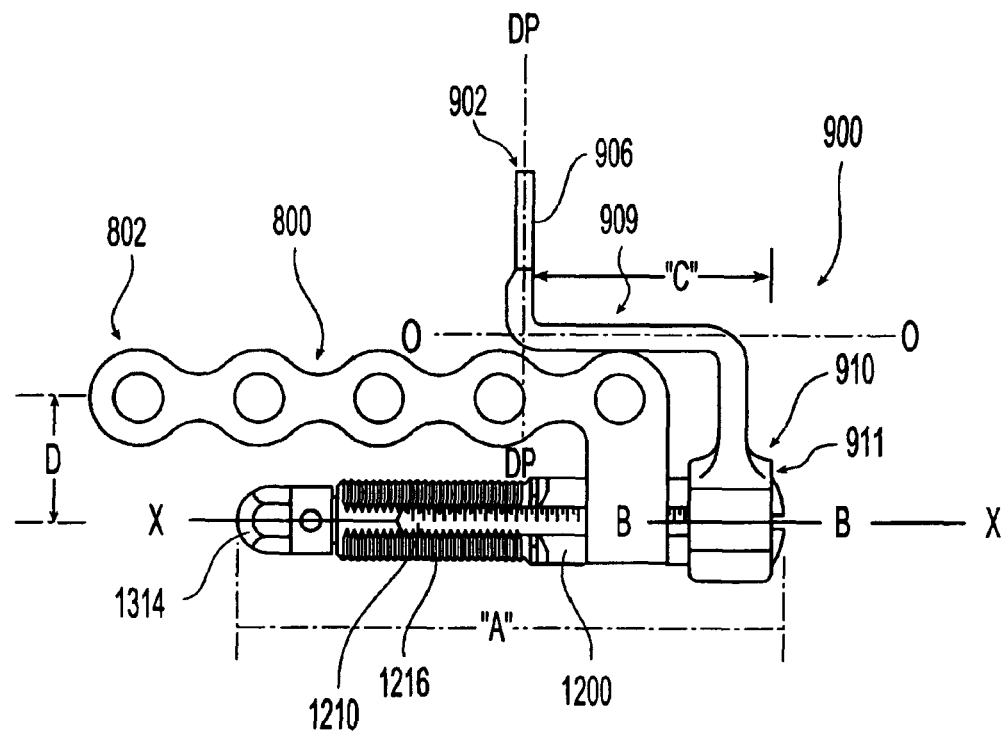
FIGS. 11a and 11b are side elevation and front elevation views, respectively, of the system illustrated in FIG. 10.
Figure 11B:
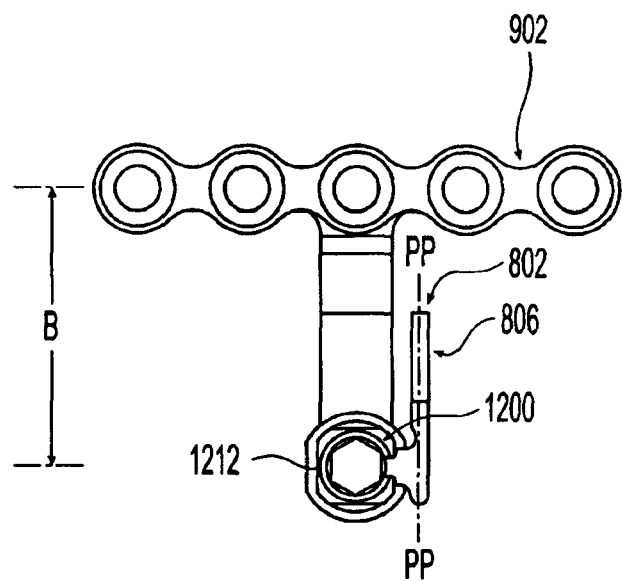

FIGS. 10, 11a and 11b illustrate an alternative embodiment of a compact maxillary distractor in which activation of the device results in no overall change in the length "A" of the device 1000. The device 1000 of this embodiment generally comprises proximal and distal footplates 800, 900 connected by an actuator 1100 having a longitudinal axis "X—X." The proximal footplate 800, connects to the patient's maxilla 21, while the distal footplate 900 connects to the patient's zygoma 22. Bone screws or other suitable fasteners may be used to fix the footplates to the respective bone segments.

Figure 12A:
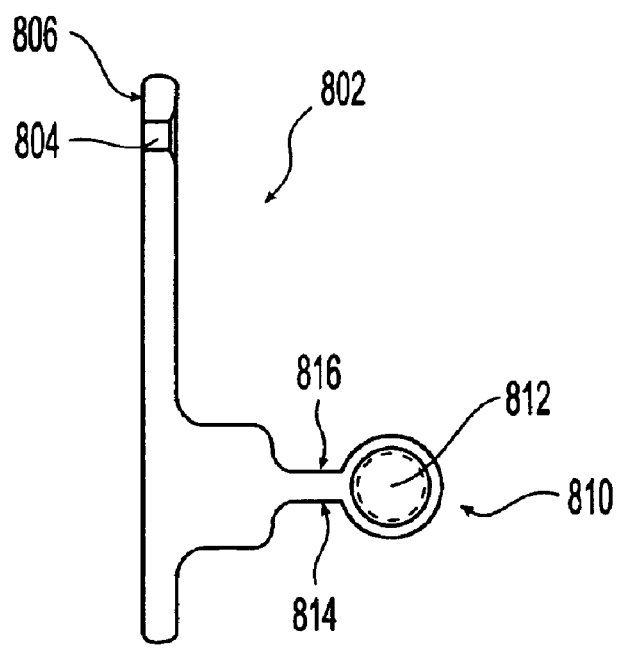
FIGS. 12a and 12b are front and side sectional views, respectively of the proximal and distal footplate actuator connecting portions.
Figure 12B:
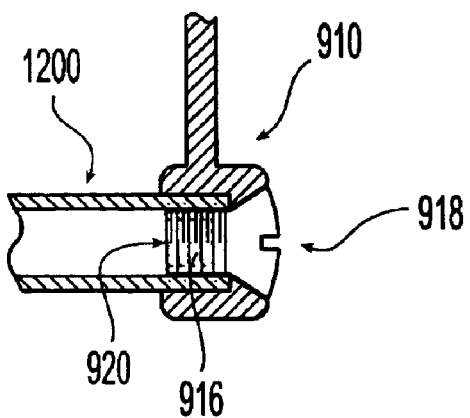

As can be seen in FIGS. 10, 12a and 12b the proximal footplate 800 has a bone attachment portion 802 and an actuator engagement portion 810. The bone attachment portion 802 comprises at least one screw hole 804, and preferably multiple screw holes 804, suitable for the insertion of a bone screw or similar fastening device. The at least one screw hole 804 may be countersunk to reduce the height of projection of the screw head above the footplate surface after the device is implanted. The proximal footplate bone attachment portion 802 further has a bone contacting surface 806 that defines a plane "PP—PP" which is oriented substantially parallel to the patient's sagittal plane, and to the longitudinal axis "X—X" of the actuator 1100. The actuator engagement portion 810 comprises a threaded bore 812 configured to engage corresponding external threads 1306 of the actuator lead screw 1300. The bone attachment and actuator engagement portions 802, 810 are joined by an outer sleeve-engaging portion 814 which comprises a reduced thickness, or "necked," region 816, configured to be received within a longitudinal slot 1210 in the actuator outer sleeve 1200.

Figure 14A:
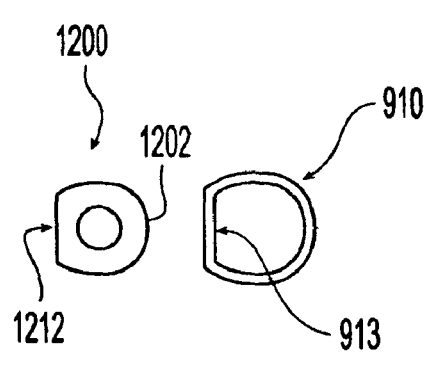
FIGS. 14a and 14b are end sectional views of two embodiments of outer sleeve and distal footplate combinations of a distractor of FIG. 10 showing corresponding profiles used to rotationally lock the pieces together.
Figure 14B:
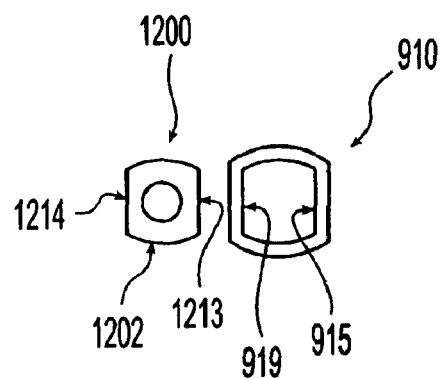

The distal footplate 900 has a bone attachment portion 902 and an actuator engagement portion 910. The bone attachment portion 902 comprises at least one screw hole 904, and preferably multiple screw holes 940, suitable for the insertion of a bone screw or similar fastening device. The at least one screw hole 904 may be countersunk to reduce the height of projection of the screw head above the footplate surface after the device is implanted. The distal footplate bone attachment portion 902 further has a bone contacting surface 906 that defines a plane "DP—DP" which is oriented substantially perpendicular to the patient's sagittal plane "SP—SP," to the proximal footplate bone contacting surface plane "PP—PP" and to the longitudinal axis "X—X" of the actuator 1100. As shown more clearly in FIGS. 12b, 14a and 14b, the distal footplate actuator engagement portion 910 comprises a bore 912 configured to engage the distal end 1206 of the actuator outer sleeve 1200.

Figure 13:
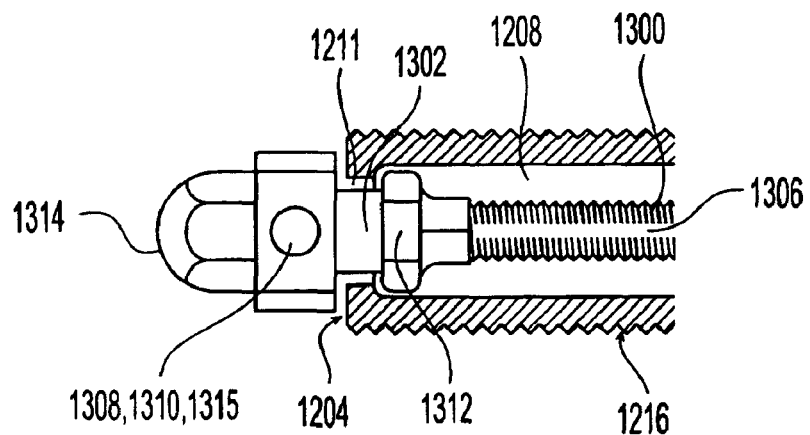
FIG. 13 is a side sectional view of the lead screw and the outer sleeve of a distractor of the system illustrated in FIG. 10.

As is shown in FIGS. 10 and 13, the actuator assembly 1100 comprises a lead screw 1300 and an outer sleeve 1200, connected in a manner similar to that described for the actuator illustrated in FIGS. 1–9. The lead screw 1300 is journaled within the outer sleeve 1200 so that the screw can rotate, but not translate axially relative to the outer sleeve. The lead screw 1300 has proximal and distal ends 1302, 1304, and a length "SL." A portion of the lead screw outer surface comprises external threads 1306 configured to engage the internally threaded bore 812 of the proximal footplate actuator attachment portion 810. The lead screw proximal end 1302 is unthreaded, and has a transverse hole 1308 suitable for the insertion of a pin 1310. An increased diameter portion 1312 is spaced a distance away from the hole 1308, such that the hole 1308 is located between the increased diameter portion 1312 and the proximal end 1302 of the lead screw 1300.

The outer sleeve 1200 has proximal and distal ends 1204, 1206, with an internal cavity defined by outer sleeve proximal and distal end bores 1211, 1208 that may encompass the entire length "SL" of the lead screw 1300, with the exception of the proximal end 1302. The outer sleeve proximal end 1204 comprises a bore 1211 sized to allow the lead screw proximal end 1302 to extend therethrough when the lead screw proximal end 1302 is completely inserted into the distal end 1206 of the outer sleeve 1200. The outer sleeve proximal end bore 1211 is sized to be smaller than the increased diameter portion of the lead screw 1312, so that when the lead screw 1300 is fully inserted into the outer sleeve 1200, the lead screw proximal end 1302 may extend out from the bore 1211 in the outer sleeve proximal end 1204.

A hex cap 1314 may be placed over the portion of the lead screw proximal end 1302 that extends beyond the outer sleeve proximal end 1204, and the cap and lead screw may be pinned together with a pin 1310 or dowel inserted through corresponding holes in the two pieces 1315, 1308. The hex cap 1314 is sized to be larger than the outer sleeve proximal end bore 1211, so that upon pinning, the lead screw proximal end 1302 may not retract into the outer sleeve.

Thus, when fully assembled, the outer sleeve proximal end bore 1211 is axially captured between the increased diameter portion of the lead screw 1312 and the hex cap 1314. This arrangement prevents axial movement of the lead screw 1300 with respect to the outer sleeve 1200, but permits relative rotational movement between the two.

As shown in FIGS. 10, 12b, 14a and 14b, the distal footplate actuator engagement portion 910 comprises a bore 912 configured to engage the outside surface 1202 of the distal end 1206 of the outer sleeve 1200. In one embodiment the bore 912 may slide onto a portion of the outer sleeve distal end 1206. The outer surface 1202 of the outer sleeve distal end 1206 may have a keyed profile, and the bore 912 of distal footplate actuator engaging portion 910 may have a corresponding keyway profile, so that when the footplate bore 912 is slid onto the outer sleeve distal end 1206, the corresponding surface profiles engage to prevent rotational movement of the footplate 900 and outer sleeve 1200 with respect to each other. In one embodiment, the outer sleeve distal end surface 1202 has a circular profile with at least one flat portion 1212 and the distal footplate bore 912 has a corresponding circular profile with at least one flat portion 913, so that when the sleeve distal end 1206 is slid onto the footplate bore 912 the flat portions 1212, 913 correspond, thereby preventing rotation of the footplate 900 and outer sleeve 1200 with respect to each other. In another embodiment, the outer sleeve distal end surface 1202 may have a circular profile with two diametrically opposed flat portions 1213, 1214 (i.e. a "double-D" configuration) and the distal footplate bore 912 may have a corresponding internal profile with a single or two flat portions 915, 919. It will be appreciated that any other keyed profile known in the art (e.g. corresponding slots, tabs, grooves, etc.) may be employed as appropriate to maintain the distal footplate and the device actuator rotationally locked together. Further, other arrangements known to those of ordinary skill in the art which actually pin the inner sleeve within the outer sleeve are also contemplated.

The distal footplate actuator attachment portion bore 912 may have a center axis "B—B" (shown if FIG. 11a) that is substantially coincident with the actuator longitudinal axis "X—X." The bore 912 further may be configured to accept the body 916 of an appropriately sized machine screw 914 such that the screw 914 may be freely inserted in the bore 912 so the distal footplate is axially restrained by the interaction of the bore 912 and the screw head 918. The outer sleeve distal end 1206 bore 1208 may comprise threads sized to engage the threaded body of the machine screw 916, so that, when the distal footplate 900 and the outer sleeve distal end 1206 are fit together, and the machine screw 914 is inserted through the distal footplate bore 912, tightening of the screw 914 may serve to axially fix the footplate 900 and outer sleeve 1200 together.

The actuator outer sleeve 1200 may further comprise a slot 1210 having a longitudinal axis which is substantially coexistent with the longitudinal axis of the actuator X—X. The slot 1210 is configured to slidingly receive the proximal footplate outer sleeve-engaging portion 814 when the proximal footplate 800 is threaded onto the lead screw 1300. The interaction between the slot 1210 and the sleeve-engaging portion 814 prevents the proximal footplate 800 from rotating with the lead screw 1300 when the device 1000 is actuated, thus forcing the proximal footplate 800 to translate along the lead screw 1300. The slot/footplate interaction also prevents the proximal and distal footplates 800, 900 from twisting with respect to each other during actuation.

To assemble the device 1000, the lead screw proximal end 1302 is introduced into the outer sleeve distal end 1206, and the lead screw 1300 is fully inserted into the outer sleeve 1200 so that the lead screw proximal end 1302 extends through the bore 1211 in the proximal end of the outer sleeve 1204. The hex cap 1314 is then installed over the lead screw proximal end 1302 and the pin 1310 is inserted to fix the two. The proximal footplate threaded bore 812 is aligned with the lead screw threads 1306, and the proximal footplate outer sleeve-engaging portion 814 is aligned with the outer sleeve slot 1210. Hand rotation of the hex cap 1314 then causes the lead screw 1300 to engage the proximal footplate threaded bore 812, drawing the proximal footplate 800 onto the lead screw 1300 so that the outer sleeve-engaging portion 814 engages the slot 1210 in the outer sleeve 1200. The hex cap 1314 is preferably rotated an amount sufficient to draw the proximal footplate actuator attachment portion 810 far enough into the outer sleeve distal end 1206 so that the attachment portion does not interfere with subsequent installation of the distal footplate machine screw 914. The distal footplate bore 912 is then aligned to correspond with outer surface 1202 of the outer sleeve distal end 1206, and the footplate 900 is slid onto the outer sleeve 1200. The machine screw 914 is then installed so its threads 916 engage the internally threaded bore 1208 of the outer sleeve distal end 1206. The machine screw is then tightened to fix the distal footplate 900 and the actuator 1100 tightly together. In a preferred embodiment, the machine screw 914 may comprise a bore 920 sized to accept the distal end 1304 of the lead screw 1300, so that when the distal footplate 900 is installed on the actuation assembly 1100, and the machine screw 914 is installed, the lead screw distal end 1304 may fit at least partially within the machine screw bore 920. This arrangement allows for maximum thread engagement between the machine screw 914 and the outer sleeve 1200 while maintaining the overall length "A" of the device as small as possible.

The easy interconnectivity of the elements of the device of this embodiment allows a surgeon to select from several actuator lengths and several footplate sizes so as to customize the device to fit the specific anatomical proportions of an individual patient. Advantageously, the actuator 1100 and footplates 800, 900 are removably engageable so that the appropriately sized pieces may be selected by the surgeon at any time prior to installation of the device in the patient. The pieces are interchangeable simply by unthreading the appropriate connection (e.g. the proximal footplate threaded bore 812 from the lead screw 1300, or the distal footplate machine screw 914 from the outer sleeve internally threaded bore 1208), then rebuilding the device using the desired piece or pieces.

The device of the current embodiment is installed at the osteotomy site (see FIG. 1) the same as the device of FIG. 2. The proximal footplate 800 is attached to the patient's maxilla 21 and the distal footplate 900 is attached to the zygoma 22. Upon installation, rotation of the hex cap 1314 in the appropriate direction causes the lead screw 1300 to turn, which in turn causes the proximal footplate 800 to translate along the lead screw 1300 in the direction away from the distal footplate 900. As the proximal footplate 800 moves along the lead screw 1300, the outer sleeve-engagement portion 814 slides within the slot 1210 in the outer sleeve 1200. A desired separation of the maxilla 21 and zygoma 22 is thereby established. Actuation of the distractor of this embodiment results in no overall change in the length "A" of the device 1000 because separation of the footplates 800, 900 is achieved merely by the change in position of the proximal footplate 800 along the fixed length of the lead screw 1300.

The device of FIG. 10 may, in one embodiment, have a posterior footplate bone attachment portion 902 that is offset from the actuator engaging portion 910, thereby facilitating placement of the actuator 1100 farther back in the mouth compared to devices having no footplate offset. More particularly, a distal footplate having such an offset configuration, shown in FIGS. 10 and 11a, allows placement of at least a portion of the actuator 1100 under the zygoma 22. This placement reduces the amount of space taken up by the device in the patient's mouth, and also facilitates the installation of longer actuator elements in patients whose anatomy or condition requires using a larger distraction vector. In one embodiment, the distal footplate offset allows the use of an actuator 1100 capable of producing a distraction vector that is in a range of from between about 10 mm to about 25 mm.

The distal footplate 900 of this embodiment comprises an actuator engagement portion 910 and a bone attachment portion 902. As can be seen in FIGS. 10 and 11a, the bone attachment and actuator engagement portions 902, 910 are joined by a substantially horizontal intermediate portion 909 having a longitudinal axis "O—O" that is oriented substantially parallel to the longitudinal axis X—X of the actuator 1100. The bone attachment portion 902 has a bone contacting surface 906 that forms a plane which, as in the earlier described embodiments, is substantially perpendicular to the longitudinal axis "X—X" of the device 1000. The offset in the distal footplate attributable to the horizontal intermediate portion 909 causes the actuator engagement portion 910 to lie outside of the plane created by the footplate bone contacting surface 906. It also causes the bone attachment portion 902 to be located closer to the proximal end of the device 1000 than the actuator engagement portion 910.

In a preferred embodiment, the intermediate portion 909 is sized so that the distance "C" between the distal end 911 of the distal footplate actuator engaging portion 910 and the distal footplate bone contacting surface 906 is in a range from between about 1 mm to about 25 mm; more preferably this range is from between about 7 mm to about 12 mm, depending on the size of the patient in whom the device will be installed. In a further preferred embodiment, the vertical distance "B" between the actuator longitudinal axis "X—X" and the distal footplate screw holes 904 is in a range from between about 5 mm to about 35 mm; more preferably this range is from between about 16.5 mm to about 26.5 mm. The vertical distance "D" between the actuator longitudinal axis "X—,", and the proximal footplate screw holes 804 is in a range from between 0 mm to about 20 mm; more preferably, this range is from between 6 mm to about 14 mm. The horizontal length "A" of the device 1000 is in a range from between 26 mm to about 43 mm.

While the described intermediate portion 909 comprises a substantially horizontal geometry, it will be obvious to one of skill in the art that the intermediate portion 909 may embrace various other geometries (e.g. angled, curved, stepped, etc.) to provide the desired offset between the bone attachment and actuator engagement portions 902, 910.

The proximal and distal footplates 800, 900 may be made of any biocompatible metal (e.g. titanium), plastic or composites. The footplates also may be made of a bioresorbable material. Where bioresorbable footplates are used, the bone screws used to attach the footplates to the patient's bone may also be made of bioresorbable material. In such a case, the bone screws should be made of a material that takes at least as long to absorb as the footplate material, thus ensuring that the footplates are secured until absorbed fully by the body.

The proximal and distal footplates 800, 900 may also be formable, to allow the surgeon to shape them to conform to the unique anatomy of the patient's bone.

As previously discussed with regard to the embodiments illustrated in FIGS. 1–9, the device of the present embodiment need not be attached directly to the patient's maxilla 21, but instead may be attached to a construct, such as a dental splint, which is attached to the maxilla 21. A typical dental splint may consist of a disk of acrylic fitted or wired to the patient's teeth and can be used when the maxilla 21 of the patient cannot support the bone screws used to support the footplate 800.

Figure 15A:
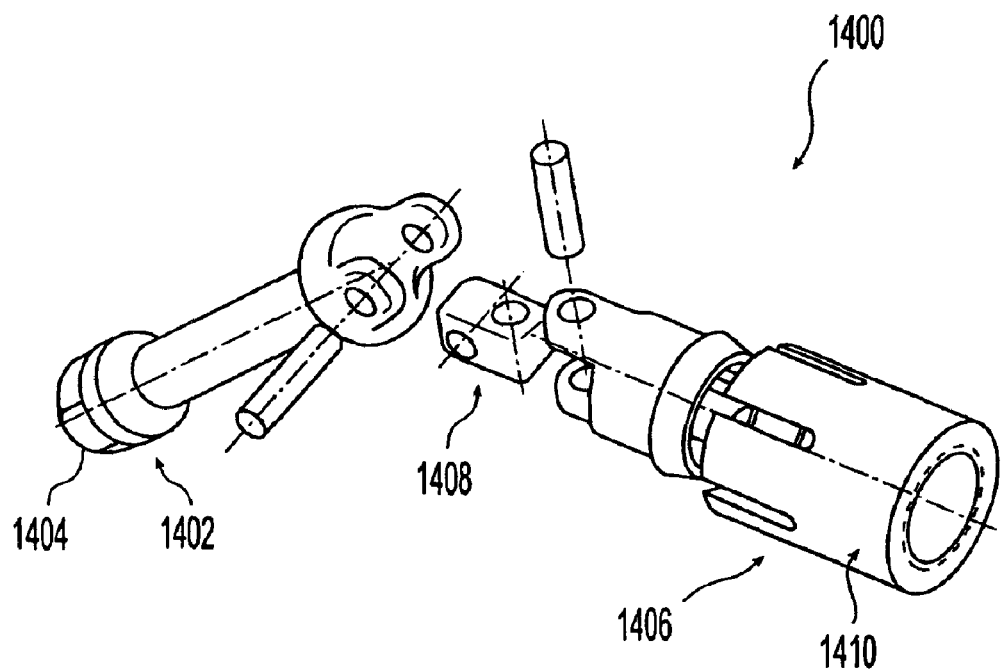
FIGS. 15a and 15b are an exploded perspective and a side elevation view of an actuation adapter for use with the system of FIG. 10.
Figure 15B:
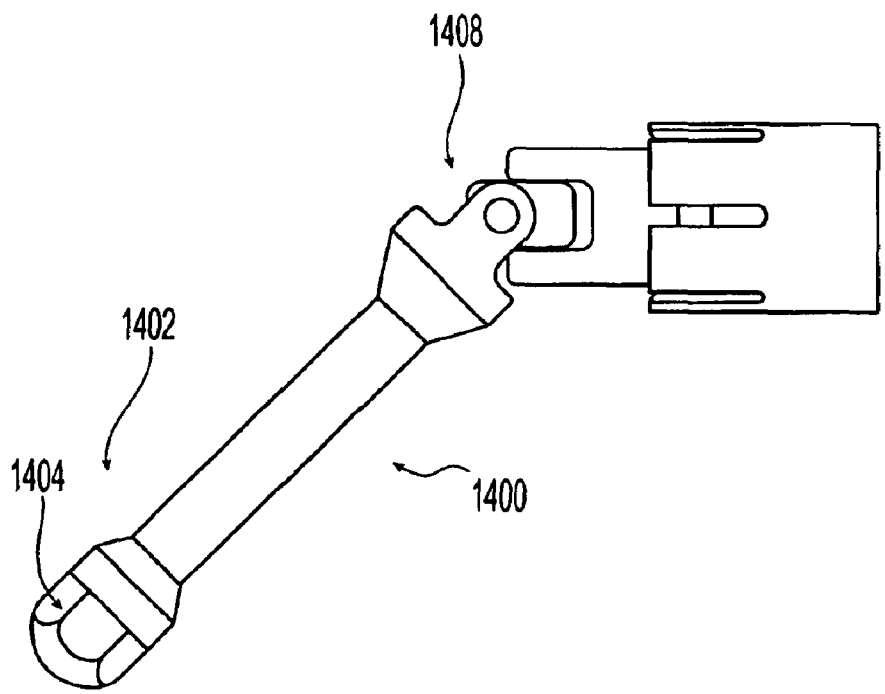

The device 1000 of the present embodiment allows placement of the actuator 1100 farther back into the oral cavity of the patient. FIGS. 15a, 15b show an adapter 1400 which may be used to extend the device actuation point (e.g. the hex cap 1314) forward to allow easy access with a tool such as a screwdriver. Such an adapter 1400 may have a proximal end 1402 comprising a hex or other similar tool head 1404, a distal end 1406 comprising a hex socket 1410 configured to engage hex cap 1314, and an intermediate universal joint 1408 configured to transmit a rotational input from the tool head 1404 to the hex socket 1410 while accommodating varying angles between the ends 1402, 1406. The adapter 1400 may be configured for permanent attachment to the device hex cap 1314, and as such would reside within the patient's mouth during the length of the distraction procedure. Alternatively, the adapter 1400 may be configured for temporary attachment to the hex cap 1314, and as such would be installed and used during the actual actuation process only. The adapter likewise may consist of various other temporary or permanent arrangements, for example the actuator may comprise a flexible rod attachment, or it could be a rigid adapter. It will be obvious that any kind of extension device known in the art may be used as appropriate to facilitate movement of the actuation point as far forward in the patient's mouth as practical for operation and to suit the comfort of the patient.

The device of FIGS. 10–14 may be installed in a patient, actuated and removed using the same method as described previously with regard to the embodiments illustrated in FIGS. 1–9. Furthermore, and as discussed above, actuation of the device may include the step of installing a universal or other type adapter which temporarily or permanently relocates the actuation point of the device In a further embodiment of the device of FIGS. 10 through 14b, the outer sleeve may be configured to accept a temporary alignment element for use in assuring proper fit and alignment of the device in a patient prior to final installation. In this embodiment, the outer sleeve 1200 may incorporate external threads 1216 configured to engage corresponding internal threads of a temporary alignment element. The alignment element may comprise a tube or rod having a length, an engagement end having internal threads corresponding to the threads of the outer sleeve 1216, and a longitudinal axis coincident to the longitudinal axis "X—X" of the device actuator 1100 upon engagement with the outer sleeve. The alignment element should be long enough to allow a portion of the element to extend out from the patient's mouth when the device is initially fit to the patient. During this initial fitting step, the alignment element allows the surgeon to easily verify or take measurements of the expected distraction vector from outside the patient, prior to final attachment of the device to the maxilla and zygoma 21, 22. The alignment element may also be used by the surgeon as a convenient handle to hold the device during placement.

The device of the above described embodiments may also be provided in the form of a kit. The kit may comprise a plurality of proximal and distal footplates 800, 900, as well as a plurality of actuation assembly 1100. The kit may be provided with proximal footplates 800 having various individual or similar shapes, sizes, number of screw holes, material or other pertinent features. Likewise, the kit may be provided with distal footplates 900 having various individual or similar shapes, sizes, number of screw holes, material or other pertinent features. In particular, the plurality of distal footplates 900 may each have a different sized intermediate portion 909 so that each distal footplate 900 may provide a different distance "C" between the distal end 911 of the distal footplate actuator engaging portion 910 and the distal footplate bone contacting surface 906. Additionally, the kit may be provided with a plurality of actuation assemblies 1100, each configured to provide a unique distraction length.

The footplates 800, 900 may attach to the actuation assembly 1100 using easily removable and connectable threaded connections. The pieces are interchangeable simply by unthreading the appropriate connection (e.g. the proximal footplate threaded bore 812 from the lead screw 1300, or the distal footplate machine screw 914 from the outer sleeve internally threaded bore 1208), then rebuilding the device using the desired piece or pieces. This easy interchangeability allows the surgeon to select from a wide variety of footplate sizes and geometries, as well as distraction vector lengths, to build a customized distractor to conform to the individual anatomy of a particular patient.

It should be emphasized that the above described embodiments of the present invention are merely specific examples adapted for specific application in the human skeletal system and should not be used to limit the claims. Modifications appropriate for other applications may readily be realized by those who are skilled in the art and who have been equipped with the understanding of the structure and operation of the present invention as set forth in the above description.

What is claimed is:

1. An orthopedic device for separating first and second bone segments, the device comprising:
   a first footplate comprising:
      a bone attachment portion having a bone contacting surface defining a first plane, and
      an actuator engaging portion;
   a second footplate comprising:
      a bone attachment portion having a bone contacting surface defining a second plane substantially perpendicular to the first plane, and
      an actuator attachment portion, and
   an actuator having a longitudinal axis and configured and adapted to be attached to the first bone segment using the first footplate and to the second bone segment using the second footplate,
   wherein the second plane is substantially perpendicular to the longitudinal axis, and the actuator attachment portion lies at a predetermined distance from the second plane.

2. The orthopedic device of claim 1, wherein the predetermined distance is in a range from between about 1 millimeter (mm) to about 25 mm.

3. The orthopedic device of claim 1, wherein the predetermined distance is in a range from between about 7 mm to about 12 mm.

4. The orthopedic device of claim 1, wherein the orthopedic device is a distractor.

5. The orthopedic device of claim 1, wherein at least one of said footplates is deformable to allow shaping in the surface of the bone segments.

6. The orthopedic device of claim 1, wherein the first sod second footplate bone attachment portions each have at least one hole configured to accept at least one bone screw for attaching the respective footplate to bone.

7. The orthopedic device of claim 6, wherein at least one of said footplates is made of a bioresorbable material.

8. The orthopedic device of claim 1, wherein the first footplate is configured and adapted to attach to the first bone segment and the second footplate is configured and adapted to attach to a construct, the construct being mechanically coupled to the patient's teeth.

9. The orthopedic device of claim 1 further comprising a screw to removably fix the second footplate to the actuator, the screw having a head and a threaded portion.

10. The orthopedic device of claim 9, wherein the second footplate attachment portion further comprises a bore having a shoulder and the actuator further comprises a distal end having a threaded bore, and the second footplate actuator attachment portion engages the actuator, and the threaded portion of the screw is inserted through the second footplate attachment portion bore and engages the threaded bore of the actuator.

11. The orthopedic device of claim 1, wherein:
   the actuator further comprises an advancement screw having external threading, and an outer sleeve having an axial slot and a second footplate engagement portion, the second footplate being coupled to the second footplate engagement portion; and
   the first footplate an actuator engaging portion having an internally threaded bore and an outer sleeve slot engaging portion, the first footplate bore interacting with the advancement screw, and the first footplate outer sleeve slot engaging portion interacting with the outer sleeve slot;
   wherein the advancement screw and the outer sleeve are associated such that only relative rotational movement about the longitudinal axis is permitted, such that rotation of the advancement screw causes movement of the first footplate with respect to the outer sleeve along the longitudinal axis.

12. The device of claim 11, wherein the first footplate is configured to attach to the maxilla and the second footplate is configured to attach to the zygoma.

13. The orthopedic device of claim 1, further comprising a temporary alignment member having a surface, wherein the actuator has an outer surface, the actuator outer surface configured to engage a the temporary alignment member surface for aligning the device prior to attachment to the bone segments, and further wherein the device is configured to be installed intra-orally.

14. The orthopedic device of claim 13, wherein the actuator outer surface comprises threads configured to match internal threads on the temporary alignment member surface.

15. The orthopedic device of claim 13, wherein the actuator outer surface is keyed to the temporary alignment member surface.

16. The orthopedic device of claim 13, wherein at least a portion of the temporary alignment member comprises a tubular element.

17. The orthopedic device of claim 13, wherein at least a portion of the temporary alignment member comprises a rod.

18. The orthopedic device of claim 13, wherein the temporary alignment member is configured such that when the alignment member is engaged with the orthopedic device and the distraction assembly is attached to the bone segments, at least a portion of the alignment member extends out of the patient's mouth.

19. The orthopedic device of claim 13, the temporary alignment member further comprising a gripping surface configured so that when the member is engaged with the orthopedic device, an operator may manipulate the position of the device by engaging the gripping surface.

20. The orthopedic device of claim 13, wherein at least a portion of the temporary alignment member comprises a tubular element.

21. The orthopedic device of claim 13, wherein at least a portion of the temporary alignment member comprises a rod.

22. The orthopedic device of claim 13, wherein the temporary alignment member is configured such that when the alignment member is engaged with the orthopedic device and the distraction assembly is attached to the bone segments, at least a portion of the alignment member extends our of the patient's mouth.

23. The orthopedic device of claim 13, the temporary alignment member further comprising a gripping surface configured so that when the member is engaged with the orthopedic device, an operator may manipulate the position of the device by engaging the gripping surface.

24. The orthopedic device of claim 13, further comprising an actuator extension member associated with the first end of the actuator, the actuator extension configured to allow a user to actuate the actuator at a position remote from the first end of the selected actuator.

25. The orthopedic device of claim 24, the actuator extension further comprising a device end and a tool end, the device end configured to engage the first end of the actuator and the tool end configured to engage a tool for actuating the actuator.

26. The orthopedic device of claim 24, wherein the actuator extension comprises a flexible member.

27. The orthopedic device of claim 24, wherein the actuator extension comprises a universal joint.

28. The orthopedic device of claim 24, wherein the actuator extension is permanently connectable to the actuator.

29. The orthopedic device of claim 24, wherein the actuator extension is removably connectable to the actuator.

30. An orthopedic device for modifying the distance between first and second bone segments of a patient, the system should be device comprising:

a first footplate for subcutaneous implantation and attachment to the first bone segment, the first footplate having bone attachment and actuator attachment portions, a second footplate for subcutaneous implantation and attachment to the second bone segment, the second footplate having bone attachment and actuator attachment portions, and a first actuator having first and second ends, and a first maximum distraction length, at least a second actuator having first and second ends, and a second maximum distraction length, the first and second maximum distraction lengths being unequal, wherein the second footplate actuator attachment portion is configured to be removably engageable with a selected one of the first and second actuators to allow attachment thereto, and wherein the first footplate actuator attachment portion engages the selected actuator between the selected actuator first and second ends, and the second footplate actuator attachment position engages the selected actuator substantially adjacent to or at the second end;

wherein the orthopedic device is a distractor and wherein the second footplate and the selected actuator are keyed to prevent rotational movement between the footplate and the actuator.

31. The orthopedic device of claim 30 further comprising a screw to removably fix the second footplate to the selected actuator, the screw having a head and a threaded portion.

32. The orthopedic device of claim 31, wherein the second footplate attachment portion further comprises a bore having a shoulder and the selected actuator further comprises a distal end having a threaded bore, the second footplate actuator attachment portion engages the selected actuator, and the threaded portion of the screw is inserted through the second footplate attachment portion bore and engages the threaded bore of the actuator.

33. The orthopedic device of claim 30, wherein the second footplate is configured and adapted to attach to the second bone segment and the first footplate is configured and adapted to attach to a construct, the construct being mechanically coupled to the patient's teeth.

34. The orthopedic device of claim 30, wherein the footplates are made of a bioresorbable material, and the selected actuator is made of a non-bioresorbable material.

35. The orthopedic device of claim 30, wherein the selected actuator comprises:

an advancement screw having external threading, an outer sleeve having an axial slot and a second footplate engagement portion, the second footplate coupled to the second footplate engagement portion; the advancement screw and outer sleeve associated to prevent relative axial translation and to permit relative rotation between the advancement screw and the outer sleeve; and the actuator attachment portion of the first footplate having an internally threaded bore, and an outer sleeve slot engaging portion;

wherein the first footplate bore interacts with the advancement screw, and the first footplate outer sleeve slot engaging portion interacts with the outer sleeve slot such that rotation of the advancement screw causes translational movement of the first footplate relative to the outer sleeve along the longitudinal axis.

36. The orthopedic device of claim 30, the second footplate bone attachment portion positioned a second distance from the second end of the selected actuator, the orthopedic device further comprising a third footplate configured to engage the second bone segment, the third footplate having bone attachment and actuator attachment portions, the third footplate actuator attachment portion configured to be removably engageable with a selected one of the first and second actuators to allow attachment thereto, the third footplate actuator attachment portion further configured to engage the selected actuator substantially adjacent to or at the second end, the third footplate bone attachment portion positioned a third distance from the second end of the selected actuator, wherein the second and third distances are substantially unequal.

37. The orthopedic device of claim 36, the selected actuator having a longitudinal axis, the second and third distances each having a first component substantially parallel to the actuator longitudinal axis and a second component substantially perpendicular to the actuator longitudinal axis, the first component of the second distance being substantially unequal to the first component of the third distance.

38. The orthopedic device of claim 30, further comprising an actuator extension member associated with the first end of the selected actuator, the actuator extension configured to allow a user to actuate the selected actuator at a position remote from the first end of the selected actuator.

39. The orthopedic device of claim 38, the actuator extension further comprising a device end and a tool end, the device end configured to engage the first end of the selected actuator and the tool end configured to engage a tool for actuating the selected actuator.

40. The orthopedic device of claim 38, wherein the actuator extension comprises a flexible member.

41. The orthopedic device of claim 38, wherein the actuator extension comprises a universal joint.

42. The orthopedic device of claim 38, wherein the actuator extension is permanently connectable to the selected actuator.

43. The orthopedic device of claim 38, wherein the actuator extension is removably connectable to the selected actuator.

44. A method for modifying the separation between the maxilla and zygoma of a patient comprising the steps of:
 (a) making at least one incision for access to the maxilla and zygoma;
 (b) providing a device for separating first and second bone segments, the device comprising:
  a first footplate comprising a maxilla attachment portion having a maxilla contacting surface defining a first plane, and an actuator engaging portion;
  a second footplate comprising a zygoma attachment portion having a zygoma contacting surface defining a second plane substantially perpendicular to the first plane, and an actuator attachment portion; and
  an actuator having a longitudinal axis and configured and adapted to be attached to the first bone segment using the first footplate and to the second bone segment using the second footplate;
 wherein the second plane is substantially perpendicular to the longitudinal axis, and the actuator attachment portion lies at a predetermined distance from the second plane;
 (c) mechanically coupling the device to the maxilla and zygoma so that at least a portion of the actuator is located behind the zygoma;
 (d) closing the incision;
 (e) performing distraction osteogenesis using the device;
 (f) reopening the incision;
 (g) removing the device from the patient; and
 (h) closing the incisions.

45. The method of claim 44, wherein step (b) comprises providing a distractor as the device.

46. The method of claim 44, wherein step (c) further comprises attaching the first footplate of the device to a construct which is attached to one or more of the patient's teeth.

47. The method of claim 44, wherein step (c) further comprises attaching the first and second footplates to the maxilla and zygoma using bioresorbable bone screws.

48. The method of claim 44, wherein step (c) comprises attaching the second footplate to the zygoma such that the footplate zygoma contacting surface is in a range from between about 1 mm to about 25 mm from the actuator attachment portion.

49. The method of claim 44, wherein at least a portion of the first and second footplates are bioresorbable and wherein step (f) comprises removing only the actuator of the device from the patient.

50. The method of claim 44, wherein step (c) comprises attaching the second footplate to the zygoma such that the footplate bone contacting surface is in a range from between about 7 mm to about 12 mm from the actuator attachment portion.

51. A method of distracting the maxilla from the zygoma of a patient comprising the steps of:
 (a) making at least one incision to expose the maxilla and zygoma;
 (b) selecting that and second distraction assemblies comprising first and second footplates and an actuation assembly;
 (c) aligning the first and the second distraction assemblies on the patient's maxilla and zygoma;
 (d) removing the first and second distraction assemblies from the patient;
 (e) performing an osteotomy separating the maxilla from the zygoma;
 (f) attaching the first and second distraction assemblies to the patient's zygoma using screws so that at least a portion of each assembly is located behind the zygoma;
 (g) mechanically coupling the first and second distraction assemblies to the patient's maxilla using screws;
 (h) closing the at least one incision, and leaving at least a portion of each distraction assembly exposed;
 (i) performing a distraction procedure, using the distraction assemblies to increase the separation of the maxilla from the zygoma;
 (j) allowing time for consolidation; and
 (k) removing the first and second distraction assemblies from the patient.

52. The method of claim 51, wherein said first and second footplates are made of bioresorbable material.

53. The method of claim 52, wherein steps (f) and (g) comprise attaching the first and second distraction assemblies to the patient using bioresorbable bone screws.

54. The method of claim 51, comprising the additional step, between steps (b) and (c) of installing first and second temporary alignment members on the first and second distraction assemblies.

55. The method of claim 54, wherein step (c) comprises aligning the first and second distraction assemblies on the patient's maxilla and zygoma using the first and second temporary alignment members.

56. The method of claim 51, wherein step (c) further comprises the step of installing temporary attachment screws, and step (d) further comprises the step of removing the temporary attachment screws.

57. The method of claim 56, comprising the additional step, between steps (d) and (e), of removing at least one of the temporary alignment members from its respective distraction assembly.

58. The method of claim 57, comprising the additional step, between steps (e) and (f), of attaching the at least one of the temporary alignment members to its respective distraction assembly.

59. The method of claim 58, wherein step (k) comprises removing the first and second actuation assemblies while leaving at least a portion of the footplates attached to the patient.

60. The method of claim 51, wherein step (g) comprises attaching at least one of the first footplates to at least one construct which is mechanically coupled to one or more of the patient's teeth.

61. An assembly kit for an orthopedic device comprising:
(a) at least one actuation assembly having first and second ends, and a longitudinal axis;
(b) a plurality of first footplates, each having a maxilla engaging portion and an actuator engaging portion, at least two of the first footplates having a different configuration; and
(c) a plurality of second footplates, each having a zygoma engaging portion and an actuator engaging portion, the zygoma engaging portion configured to permit at least a portion of the actuation assembly to be located behind the zygoma, at least two of the second footplates having a different configuration;
wherein at least one of the first and second footplates are interchangeably removable from the actuation assembly to allow a surgeon to build a customized device to fit an anatomy of a particular patient.

62. The kit of claim 61, wherein each first footplate maxilla engaging portion further comprises screw holes configured to accept bone screws, and the configuration of such screw holes is different for each first footplate.

63. The kit of claim 61, wherein at least two of the first footplate maxilla engaging portions comprise a different shape.

64. The kit of claim 61, wherein each second footplate zygoma engaging portion further comprises screw holes configured to accept bone screws, and the configuration of such screw holes is different for each second footplate.

65. The kit of claim 61, wherein at least two of the second footplate zygoma engaging portions further comprise a different shape.

66. The kit of claim 61, wherein each second footplate zygoma engaging portion is configured to permit the actuation assembly to be located behind the zygoma by a different amount.

67. The kit of claim 61, further comprising a screw so removably fix one of the plurality of second footplates to the actuator, the screw having a head and a threaded portion.

68. The kit of claim 67, wherein each second footplate actuator engaging portion further comprises a bore and the at least one actuator further comprises a distal end having a threaded bore, each second footplate actuator attachment portion is configured to engage the at least one actuator, and the threaded portion of the screw may be inserted through the second footplate bore to engage the threaded bore of the at least one actuator.

69. The kit of claim 61, further comprising a plurality of temporary alignment elements configured to be removably engageable with the at least one actuation assembly to permit in-situ alignment of the orthopedic device.

70. A connecting element for connecting an orthopedic device actuator to a patient's bone, the connecting element comprising:
a bone contacting portion having a bone contacting surface configured to receive at least one fastener for connecting to a bone segment;
an actuator engaging portion configured to engage the actuator along an actuation axis to couple the connecting element to the actuator; and
an offset portion for connecting the bone contacting portion and the actuator engaging portion;
wherein at least a portion of the bone contacting surface defines a plane substantially perpendicular to the actuation axis, and the actuator engagement portion lies a predetermined distance from the plane.

71. The connecting element of claim 70, the actuator engaging portion further comprises a bore having a bore axis, wherein at least a portion of the offset portion is oriented substantially parallel to the longitudinal axis.

72. The connecting element of claim 70, wherein the predetermined distance is in a range from between about 1 mm to about 25 mm.

73. The connecting element of claim 70, wherein the predetermined distance is in a range from between about 7 mm to about 12 mm.

74. The connecting element of claim 70, wherein the bone contacting portion is deformable to allow shaping to the surface of a contacted bone.

75. The connecting element of claim 70, wherein the bone contacting portion has at least one hole configured to accept at least one bone screw for attaching the connecting element to bone.

76. The connecting element of claim 70, wherein the connecting element is made of a bioresorbable material.

77. The connecting element of claim 70, wherein the bone contacting surface is configured to engage the patient's zygoma, the offset portion is configured so that the actuator engaging portion is located behind the patient's zygoma.

78. An orthopedic device for modifying the distance between first and second segments of a patient, the device comprising:
a first footplate for subcutaneous implantation and attachment to the first bone segment, the first footplate having bone attachment and actuator attachment portions.
a second footplate for subcutaneous implantation and attachment to the second bone segment, the second footplate having bone attachment and actuator attachment portions, and
a first actuator having first and second ends, and a first maximum distraction length,
at least a second actuator having first and second ends, and a second maximum distraction length, the first and second maximum distraction lengths being unequal,
wherein the second footplate actuator attachment portion is configured to be removably engageable with a selected one of the first and second actuators to allow attachment thereto, and wherein the first footplate actuator attachment portion engages the selected actuator between the selected actuator first and second ends, and the second footplate actuator attachment portion engages the selected actuator substantially adjacent to or at the second end;
wherein the orthopedic device further comprises an actuator extension member associated with the first end of the selected actuator, the actuator extension configured to allow a user to actuate the selected actuator at a position remote from the first end of the selected actuator.

79. The orthopedic device of claim 78, wherein the orthopedic device is a distractor.

80. The orthopedic device of claim 79, wherein the second footplate and the selected actuator are keyed to prevent rotational movement between the footplate and the actuator.

81. The orthopedic device of claim 79, further comprising a screw to removably fix the second footplate to the selected actuator, the screw having a head and a threaded portion.

82. The orthopedic device of claim 81, wherein the second footplate attachment portion further comprises a bore having a shoulder and the selected actuator further comprises a distal end having a threaded bore, the second footplate actuator attachment portion engages the selected actuator, and the threaded portion of the screw is inserted through the second footplate attachment portion bore and engages the threaded bore of the actuator.

83. The orthopedic device of claim 79, wherein the second footplate is configured and adapted to attach to the second bone segment and the first footplate is configured and adapted to attach to a construct, the construct being mechanically coupled to the patient's teeth.

84. The orthopedic device of claim 78, wherein the footplates are made of a bioresorbable material, and the selected actuator is made of a non-bioresorbable material.

85. The orthopedic device of claim 78, wherein the selected actuator comprises:

an advancement screw having external threading, an outer sleeve having an axial slot and a second footplate engagement portion, the second footplate coupled to the second footplate engagement portion; the advancement screw and outer sleeve associated to prevent relative axial translation and to permit relative rotation between the advancement screw and the outer sleeve; and the actuator attachment portion of the first footplate having an internally threaded bore, and an outer sleeve slot engaging portion;

wherein the first footplate bore interacts with the advancement screw, and the first footplate outer sleeve slot engaging portion interacts with the outer sleeve slot such that rotation of the advancement screw causes translational movement of the first footplate relative to the outer sleeve along the longitudinal axis.

86. The orthopedic device of claim 78, the second footplate bone attachment portion positioned a second distance from the second end of the selected actuator, the orthopedic device further comprising a third footplate configured to engage the second bone segment, the third footplate having bone attachment and actuator attachment portions, the third footplate actuator attachment portion configured to be removably engageable with a selected one of the first and second actuators to allow attachment thereto, the third footplate actuator attachment portion further configured to engage the selected actuator substantially adjacent to or at the second end, the third footplate bone attachment portion positioned a third distance from the second end of the selected actuator, wherein the second and third distances are substantially unequal.

87. The orthopedic device of claim 86, the selected actuator having a longitudinal axis, the second and third distances each having a first component substantially parallel to the actuator longitudinal axis and a second component substantially perpendicular to the actuator longitudinal axis, the first component of the second distance being substantially unequal to the first component of the third distance.

88. The orthopedic device of claim 78, the actuator extension further comprises a device end and a tool end, the device end configured to engage the first end of the selected actuator and the tool end configured to engage a tool for actuating the selected actuator.

89. The orthopedic device of claim 78, wherein the actuator extension comprises a flexible member.

90. The orthopedic device of claim 78, wherein the actuator extension comprises a universal joint.

91. The orthopedic device of claim 78, wherein the actuator extension is permanently connectable to the selected actuator.

92. The orthopedic device of claim 78, wherein the actuator extension is removably connectable to the selected actuator.

* * * * *